(12) United States Patent
Wang et al.

(10) Patent No.: US 8,323,929 B2
(45) Date of Patent: *Dec. 4, 2012

(54) METHODS FOR DETECTING NUCLEIC ACID SEQUENCE VARIATIONS

(75) Inventors: Sha-Sha Wang, Cockeysville, MD (US); Keith Thornton, Pikesville, MD (US); James G. Nadeau, Ellicott City, MD (US); Tobin J. Hellyer, Owings Mills, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 194 days.

This patent is subject to a terminal disclaimer.

(21) Appl. No.: 12/419,737

(22) Filed: Apr. 7, 2009

(65) Prior Publication Data

US 2009/0246792 A1     Oct. 1, 2009

Related U.S. Application Data

(60) Continuation of application No. 11/724,180, filed on Mar. 15, 2007, now abandoned, which is a continuation of application No. 10/202,896, filed on Jul. 26, 2002, now abandoned, which is a continuation-in-part of application No. 09/335,218, filed on Jun. 17, 1999, now abandoned, and a continuation-in-part of application No. 09/894,788, filed on Jun. 28, 2001, now Pat. No. 6,656,680, which is a division of application No. 09/590,061, filed on Jun. 8, 2000, now Pat. No. 6,316,200.

(51) Int. Cl.
  *C12P 19/34* (2006.01)
  *C12Q 1/68* (2006.01)
  *C07H 21/02* (2006.01)
  *C07H 21/04* (2006.01)
  *C07H 21/00* (2006.01)

(52) U.S. Cl. ...... 435/91.2; 435/6.1; 435/6.11; 435/6.12; 435/91.1; 536/23.1; 536/24.3; 536/24.33; 536/25.3

(58) Field of Classification Search ............. 435/6, 91.1, 435/91.2, 183, 6.1, 6.11, 6.12; 436/94, 501; 536/23.1, 24.3, 24.33, 25.3

See application file for complete search history.

(56) References Cited

U.S. PATENT DOCUMENTS

| | | | |
|---|---|---|---|
| 2,725,804 A | 12/1955 | Herzfeld | |
| 4,124,022 A | 11/1978 | Gross | |
| 4,451,130 A | 5/1984 | Yan | |
| 4,683,195 A | 7/1987 | Mullis et al. | |
| 4,851,331 A | 7/1989 | Vary et al. | |
| 4,883,750 A | 11/1989 | Whiteley et al. | |
| 4,988,617 A | 1/1991 | Landegren et al. | |
| 4,999,713 A | 3/1991 | Ueno et al. | |
| 5,115,265 A | 5/1992 | Swayze | |
| 5,270,184 A | 12/1993 | Walker et al. | |
| 5,406,413 A | 4/1995 | Mogamiya | |
| 5,407,799 A | 4/1995 | Studier | |
| 5,422,252 A | 6/1995 | Walker et al. | |
| 5,455,166 A | 10/1995 | Walker | |
| 5,479,229 A | 12/1995 | Minamikawa | |
| 5,503,980 A | 4/1996 | Cantor | |
| 5,525,494 A | 6/1996 | Newton | |
| 5,547,861 A | 8/1996 | Nadeau et al. | |
| 5,550,025 A | 8/1996 | Walker | |
| 5,578,458 A | 11/1996 | Caskey et al. | |
| 5,593,867 A | 1/1997 | Walker et al. | |
| 5,595,890 A | 1/1997 | Newton et al. | |
| 5,607,834 A | 3/1997 | Bagwell | |
| 5,641,633 A | 6/1997 | Linn et al. | |
| 5,681,705 A | 10/1997 | Schram et al. | |
| 5,691,143 A | 11/1997 | Bustos et al. | |
| 5,691,145 A | 11/1997 | Pitner et al. | |
| 5,750,341 A | 5/1998 | Macevicz | |
| 5,763,184 A | 6/1998 | Reynolds et al. | |
| 5,800,989 A | 9/1998 | Linn et al. | |
| 5,841,633 A | 11/1998 | Huang | |
| 5,846,726 A | 12/1998 | Nadeau et al. | |
| 5,866,336 A | 2/1999 | Nazarenko et al. | |
| 5,919,630 A | 7/1999 | Nadeau et al. | |
| 5,928,869 A | 7/1999 | Nadeau et al. | |
| 5,969,119 A | 10/1999 | Macevicz | |
| 6,025,130 A | 2/2000 | Thomas et al. | |
| 6,077,669 A | 6/2000 | Little et al. | |
| 6,130,047 A | 10/2000 | Nadeau et al. | |

(Continued)

FOREIGN PATENT DOCUMENTS

CA              99-1556 A1      6/1976

(Continued)

OTHER PUBLICATIONS

Bagwell, et al., "A New Homogeneous Assay System for Specific Nucleic Acid Sequences: Poly-dA and Poly-A Detection," *Nucleic Acids Research*, 1994, vol. 22, No. 12, pp. 2424-2425.

Chen et al., "Template-Directed Dye-Terminator Incorporation (TDI) Assay: A Homogenous DNA Diagnostic Method Based on Fluorescence Resonance Energy Transfer," *Nucleic Acids Research*, 1997, vol. 25, No. 2, pp. 347-353.

Drysdale, et al., "Complex Promoter and Coding Region $\beta_2$-Adrenergic Receptor Haplotypes Alter Receptor Expression and Predict In Vivo Responsiveness," *PNAS*, 2000, vol. 97, No. 19, pp. 10483-10488.

Fauser et al., "Simultaneous Detection of Multiple Point Mutations Using Fluorescence-Coupled Competitive Primer Extension," *BioTechniques*, 1997, vol. 22 No. 5, pp. 964-968.

(Continued)

*Primary Examiner* — Frank W Lu

(74) *Attorney, Agent, or Firm* — Lerner, David, Littenberg, Krumholz & Mentlik, LLP

(57) ABSTRACT

The invention employs an unlabeled signal primer comprising a 5' adapter sequence for detection of variations in nucleic acid target sequences. The detection system further comprises a reporter probe, the 3' end of which hybridizes to the complement of the 5' adapter sequence of the signal primer to produce a 5' overhang. Polymerase is used to fill in the overhang and synthesize the complement of the 5' overhang of the reporter probe. Synthesis of the reporter probe complement is detected, either directly or indirectly, as an indication of the presence of the target.

11 Claims, 17 Drawing Sheets

U.S. PATENT DOCUMENTS

| | | | |
|---|---|---|---|
| 6,166,765 | A | 12/2000 | Toyofuku |
| 6,207,379 | B1 | 3/2001 | Lee et al. |
| D442,616 | S | 5/2001 | Ohmori et al. |
| D442,617 | S | 5/2001 | Ohmori et al. |
| 6,229,569 | B1 | 5/2001 | Saito et al. |
| 6,247,855 | B1 | 6/2001 | Motohashi et al. |
| 6,251,609 | B1 | 6/2001 | Brink et al. |
| 6,258,546 | B1 | 7/2001 | McMillian et al. |
| 6,261,785 | B1 | 7/2001 | Wood et al. |
| 6,277,582 | B1 | 8/2001 | Price, Jr. et al. |
| 6,306,597 | B1 | 10/2001 | Macevicz |
| 6,309,833 | B1 | 10/2001 | Edman et al. |
| 6,316,200 | B1 | 11/2001 | Nadeau et al. |
| PP12,298 | P2 | 12/2001 | Piscator |
| 6,326,145 | B1 | 12/2001 | Whitcombe et al. |
| 6,379,888 | B1 | 4/2002 | Nadeau et al. |
| 6,414,709 | B1 | 7/2002 | Palm et al. |
| 6,656,680 | B2 | 12/2003 | Nadeau et al. |
| 6,743,582 | B2 | 6/2004 | Nadeau et al. |
| 7,223,536 | B2 | 5/2007 | Wright et al. |
| 2001/0009761 | A1 | 7/2001 | Wright et al. |
| 2001/0039334 | A1 | 11/2001 | Wright et al. |
| 2002/0021895 | A1 | 2/2002 | Kanai et al. |
| 2002/0025519 | A1 | 2/2002 | Wright et al. |
| 2002/0086306 | A1 | 7/2002 | Nadeau et al. |
| 2002/0094527 | A1 | 7/2002 | Nadeau et al. |
| 2002/0102574 | A1 | 8/2002 | Nadeau et al. |
| 2003/0165913 | A1 | 9/2003 | Wang et al. |
| 2005/0239084 | A1 | 10/2005 | Nadeau et al. |
| 2009/0131647 | A1 | 5/2009 | Nadeau et al. |
| 2009/0246792 | A1 | 10/2009 | Wang et al. |

FOREIGN PATENT DOCUMENTS

| | | |
|---|---|---|
| CA | 2306055 A1 | 12/2000 |
| CA | 2345979 A1 | 12/2001 |
| CA | 2493609 A1 | 2/2004 |
| DE | 29912683 U1 | 3/2000 |
| DE | 60029876 T2 | 2/2007 |
| DE | 60118655 T2 | 4/2007 |
| EP | 0200362 A2 | 11/1986 |
| EP | 0360940 A2 | 4/1990 |
| EP | 0395398 A2 | 10/1990 |
| EP | 0497272 A1 | 8/1992 |
| EP | 0 543 612 | 5/1993 |
| EP | 0678582 A1 | 10/1995 |
| EP | 0 684 315 | 11/1995 |
| EP | 0 881 302 | 12/1998 |
| EP | 1061135 A2 | 12/2000 |
| EP | 1087020 A2 | 3/2001 |
| EP | 1162277 A2 | 12/2001 |
| EP | 1585967 A2 | 10/2005 |
| GB | 2257597 A | 1/1993 |
| JP | 53-116215 A | 10/1978 |
| JP | 62-024555 A | 2/1987 |
| JP | 03-043308 A | 2/1991 |
| JP | 03-058578 A | 3/1991 |
| JP | 04-000287 A | 1/1992 |
| JP | 05-015439 | 3/1993 |
| JP | 93-15439 A | 3/1993 |
| JP | 07-013243 A | 1/1995 |
| JP | 7-225410 A | 8/1995 |
| JP | 9-230464 A | 9/1997 |
| JP | 2001057892 A | 3/2001 |
| JP | 2002045192 A | 2/2002 |
| JP | 200310806 A | 8/2004 |
| JP | 2006515982 T | 6/2006 |
| JP | 2008200050 A | 9/2008 |
| WO | 9201813 A1 | 2/1992 |
| WO | 9209689 A1 | 6/1992 |
| WO | 9522626 A1 | 8/1995 |
| WO | 9802449 A1 | 1/1998 |
| WO | 0061816 A1 | 10/2000 |
| WO | 0062036 A1 | 10/2000 |
| WO | 0177317 A1 | 10/2001 |
| WO | 2004011908 A2 | 2/2004 |

OTHER PUBLICATIONS

Forster, Th., "Intermolecular Energy Migration and Fluorescence," *Analytical Physics*, 1948, vol. 2, pp. 55-75.

Ghosh et al., "Real Time Kinetics of Restriction Endonuclease Cleavage Monitored by Fluorescence Resonance Energy Transfer," *Nucleic Acids Research*, 1994, vol. 22, No. 15, pp. 3155-3159.

Guatelli et al., "Isothermal, In Vitro Amplification of Nucleic Acids by a Multienzyme Reaction Modeled After Retroviral Replication," *Proc. Natl. Acad. Sci. USA*, 1990, vol. 87, pp. 1874-1878.

Kwok et al., "Effects of Primer—Template Mismatches on the Polymerase Chain Reaction: Human Immunodeficiency Virus Type 1 Model Studies," *Nucleic Acids Research*, 1990, vol. 18, No. 4, pp. 999-1005.

Kwok et al., "A Guide to the Design and Use of Mismatched and Degenerate Primers," *PCR Methods and Amplifications*, 1994, vol. 3 No. 4, pp. S39-47.

Krausa et al., "Defining the Allelic Variants of HLA-A30 in the Sardinian Population Using Amplification Refractory Mutation System-Polymerase Chain Reaction," *Human Immunology*, 1995, vol. 44, pp. 35-42.

Lee, et al., "Allelic Discrimination by Nick-Translation PCR with Fluorogenic Probes," *Nucleic Acids Research*, 1993, vol. 21, No. 16, pp. 3761-3766.

Morrison, L.E., "Detection of Energy Transfer and Fluorescence Quenching," *Nonisotopic DNA Probe Techniques*, Kricka, L.J., ed. 1992, *Academic Press, Inc.*, Chapter 13, pp. 311-352.

Newton, et al., "Analysis of Any Point Mutation in DNA. The Amplification of Refractory Mutation System (ARMS)," *Nucleic Acids Research*, 1989, vol. 17, No. 7, pp. 2503-2516.

Tyagi, et al., "Molecular Beacons: Probes that Fluoresce Upon Hybridization," *Nature Biotechnology*, 1996, vol. 14, pp. 303-308.

Ugozzoli L. et al., "Allelel Specific Polymerase chain Reaction," *Methods: A Companion to Methods in Enzymology Academic Press, Inc.*, 1991, vol. 2, No. 1, pp. 42-48.

Walker et al.,"Strand Displacement Amplification-An Isothermal, In Vitro DNA Amplification Technique", *Nucleic Acids Research*, 1992, vol. 20, No. 7, pp. 1691-1696.

Search Report EP0881302 dated Oct. 24, 2001.

Search Report for EP1061135 dated May 2, 2003.

Search Report for EP1162277 dated Oct. 25, 2002.

Little et al, Clinical Chemistry, vol. 45, No. 6, Part 1, pp. 777-784, 1999.

Krausa et al., "Defining the Allelic Variants of HLA-A30 in the Sardinian Population Using Amplification Refractory Mutation System-Polymerase Chain Reaction", ICRF, Institute of Molecular Medicine, Oxford, UK, Sep. 1995; 44(1):35-42 (Abstract only).

International Search Report of PCT/US03/023569 dated Jun. 14, 2007.

Nazarenko et al., "A closed tube format for amplification and detection of DNA on energy transfer", Nucleic Acids Research, Oxford University Press, Surrey, 68, vol. 25, No. 12, pp. 2516-2521, 1997, XP-002094959.

Neilan et al., "A universal procedure for primer labelling of amplicons", Nucleic Acids Research, Oxford University Press, vol. 25, No. 14, pp. 2938-2939, Surrey, GB, 1997, XP-001026498.

Nuovo et al., "In Situ amplification using universal energy transfer-labeled primers", The Journal of Histochemistry and Cytochemistry, vol. 47(3): pp. 273-279, 1999, XP-008002684.

Search Report for EP0543612 (Application No. EP 92310465.7) dated May 19, 2003.

Search Report for EP0684315 (Application No. EP95103569) dated Jul. 19, 1995.

Search Report for EP1585967 (Application No. EP03771988) dated Apr. 14, 2008.

Walker, "Empirical aspects of strand displacement amplification", PCR Methods and Applications, vol. 3, No. 1, pp. 1-6, Aug. 1993.

Jazwinska, E.C. (1998), Hermochromatosis: a genetic defect in iron metabolism. Bioessays, 20: 562-568. (providing Abstract only).

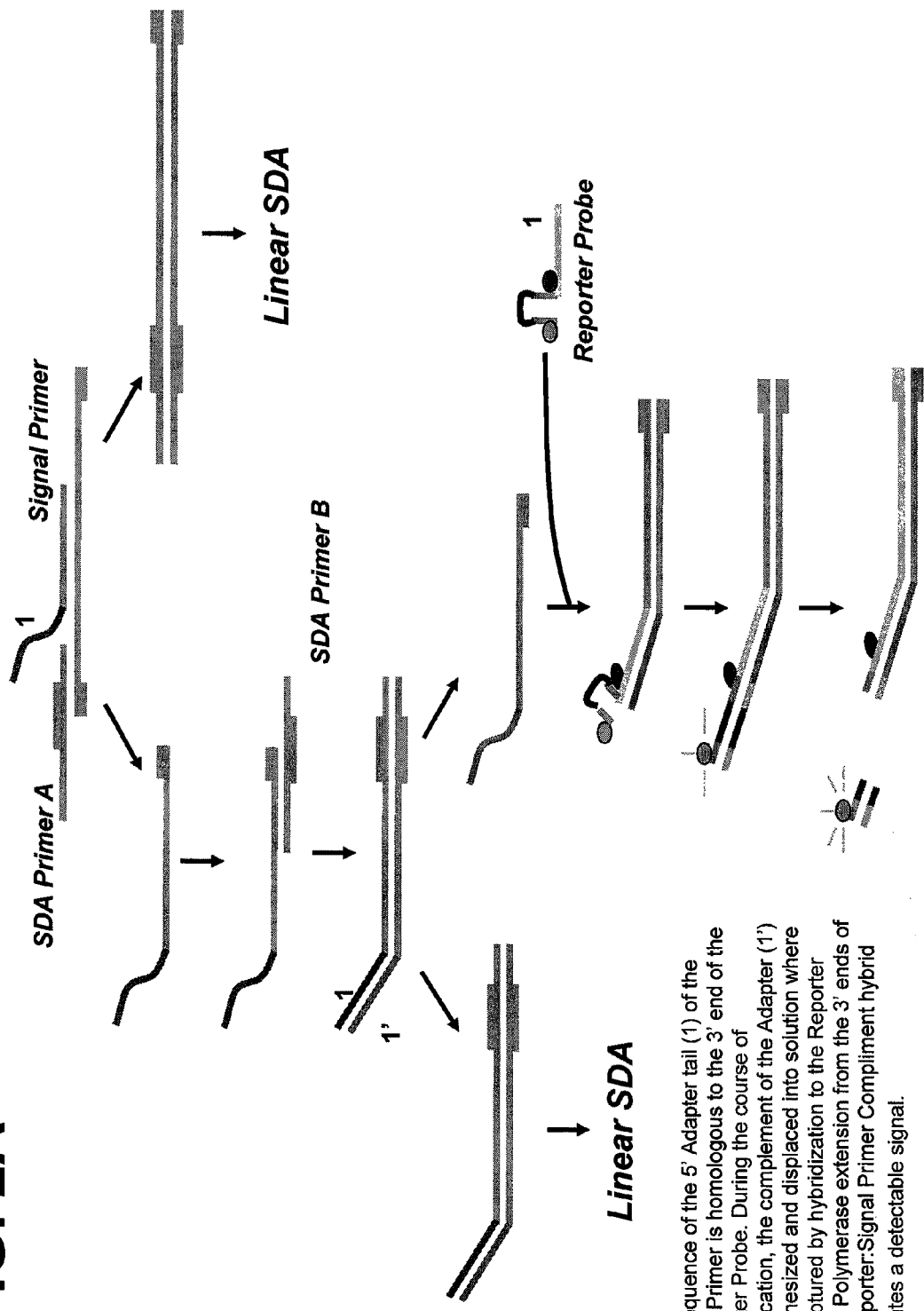

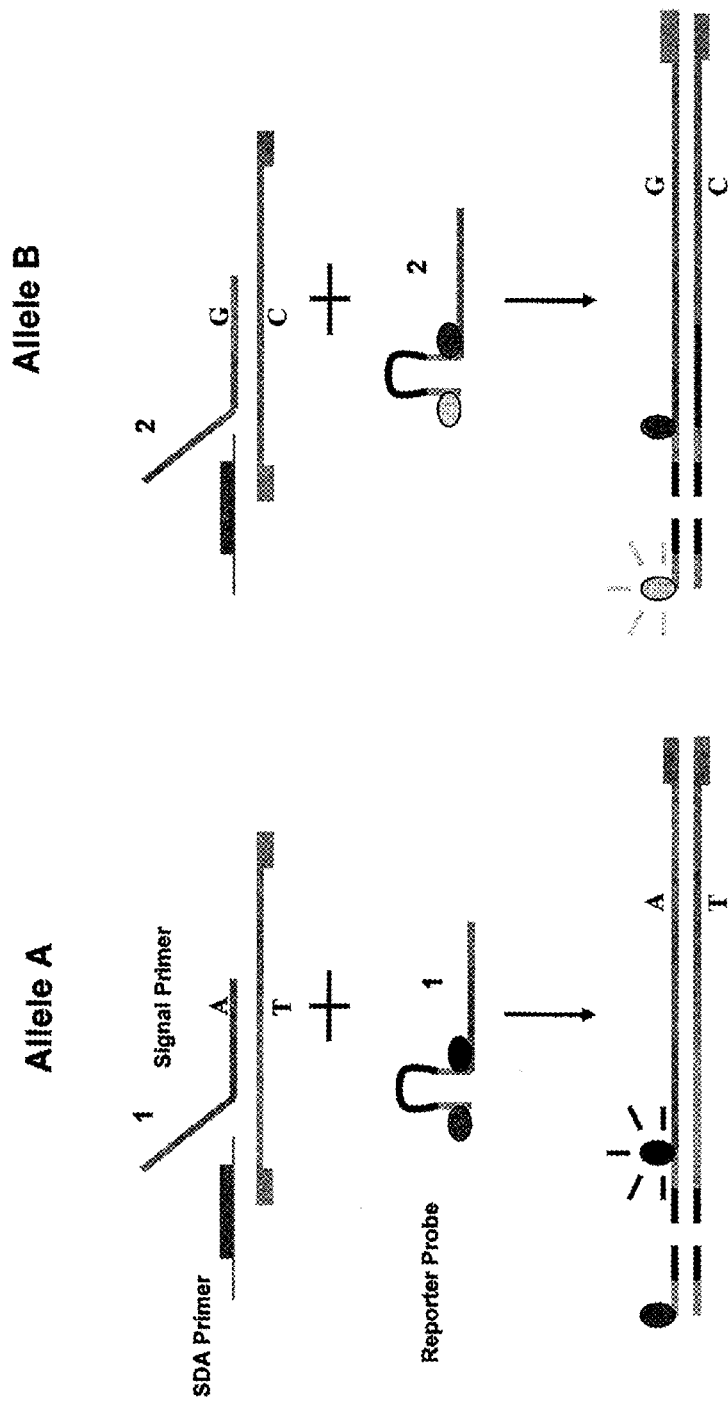

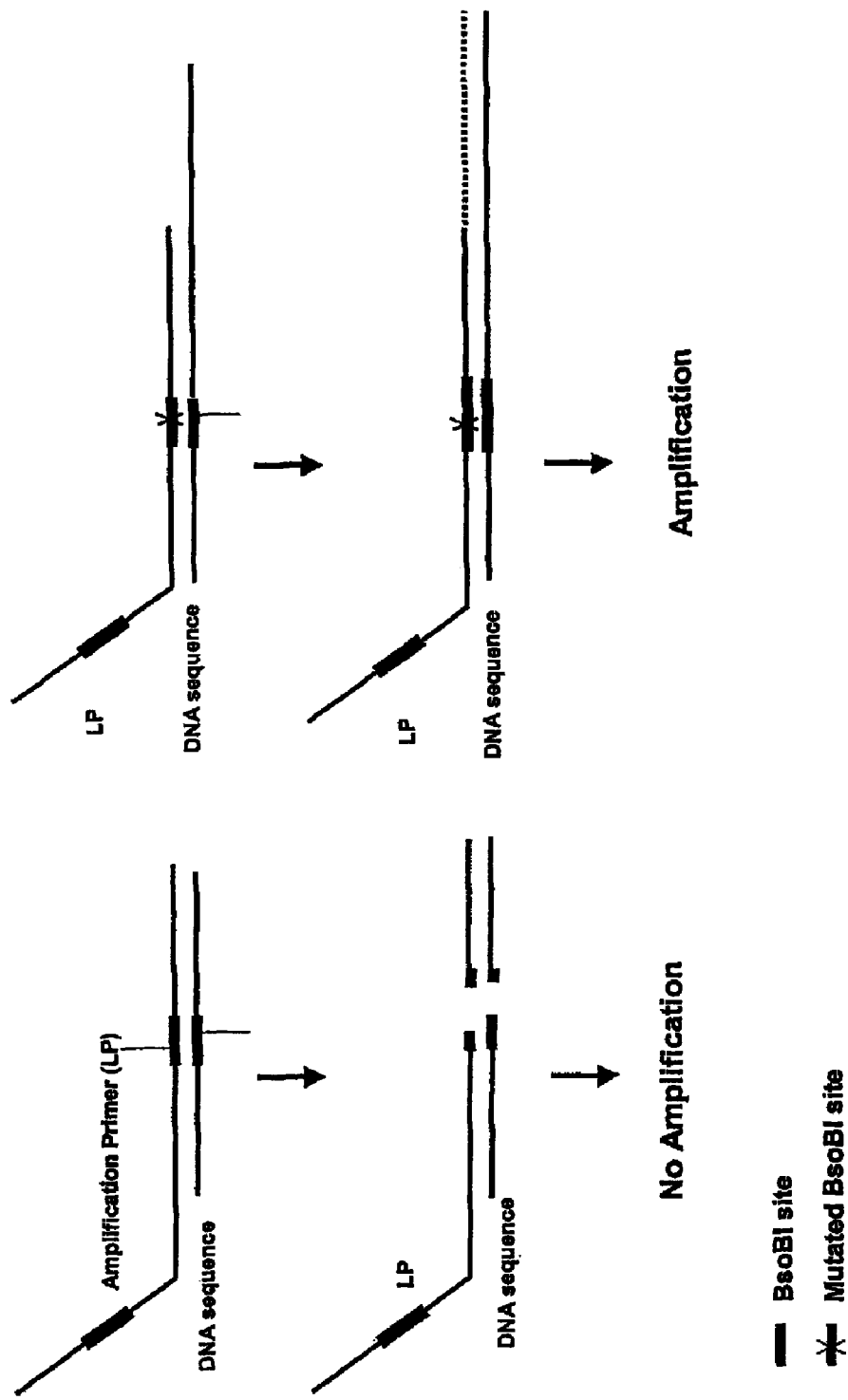

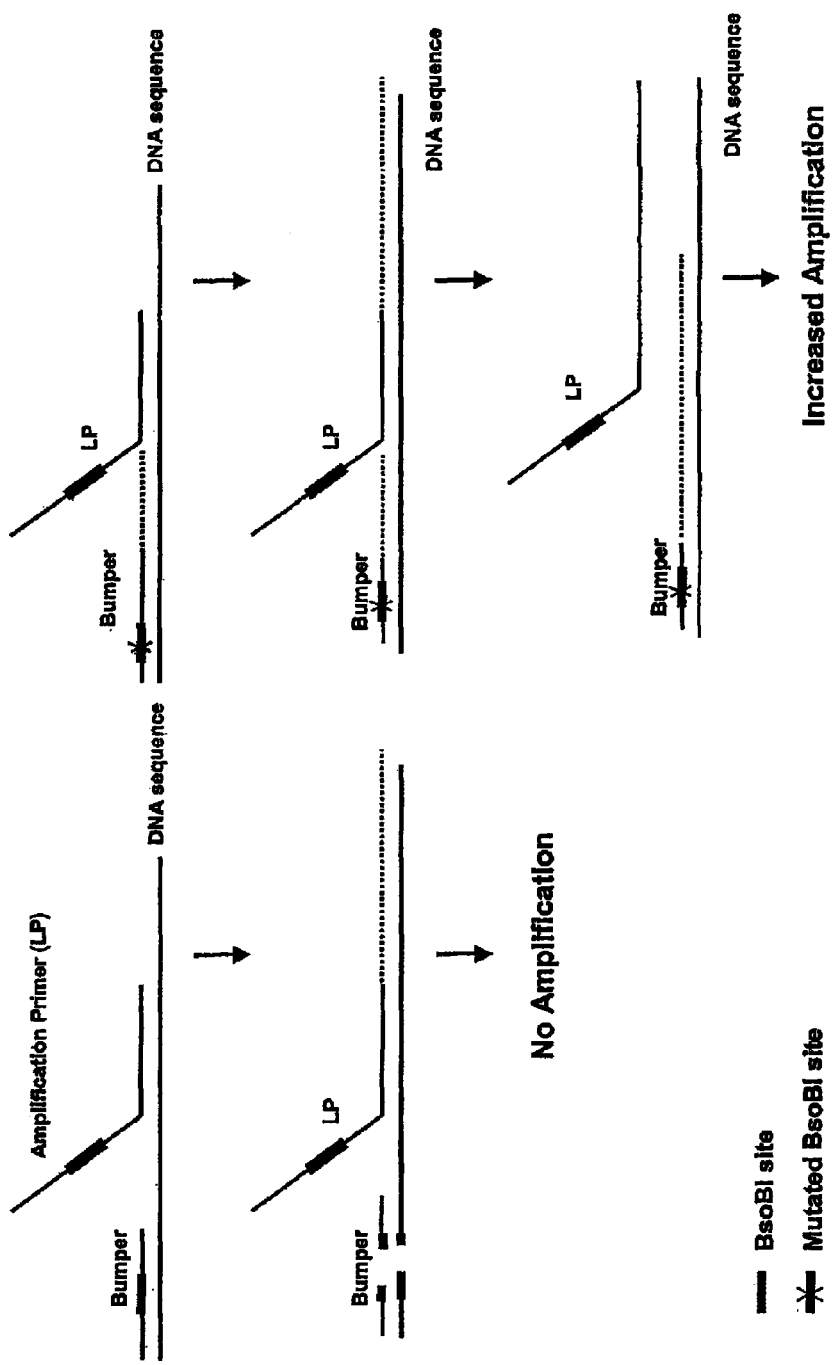

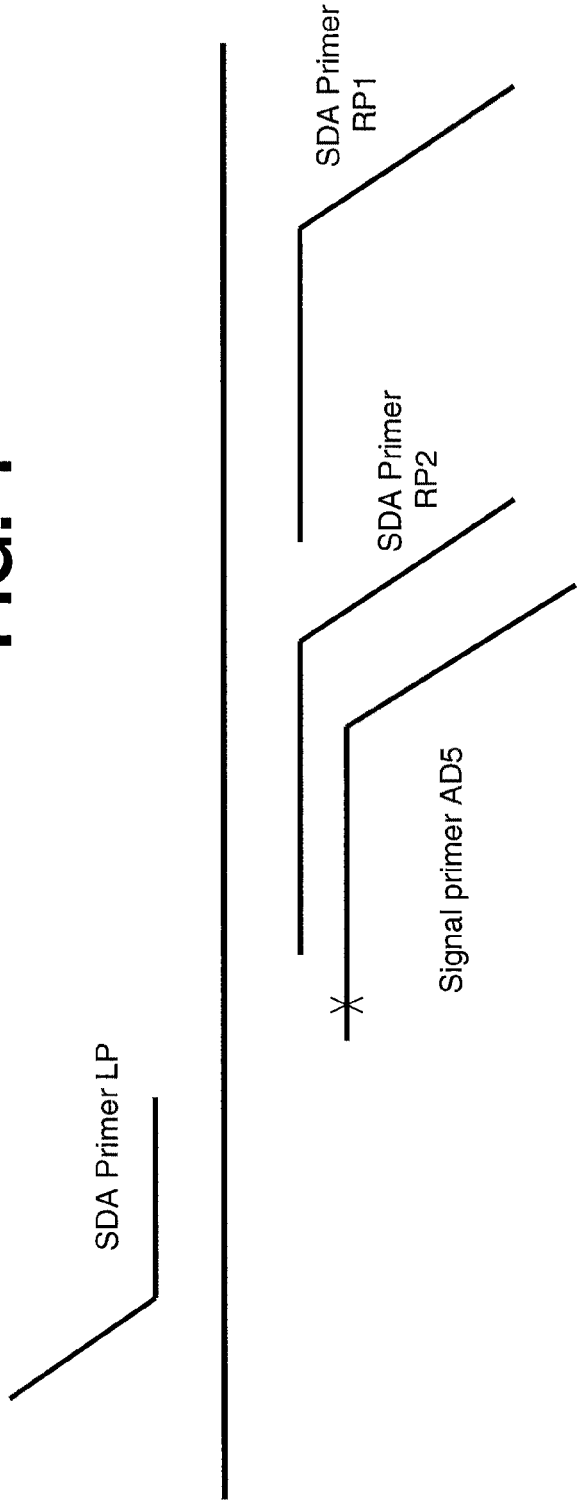

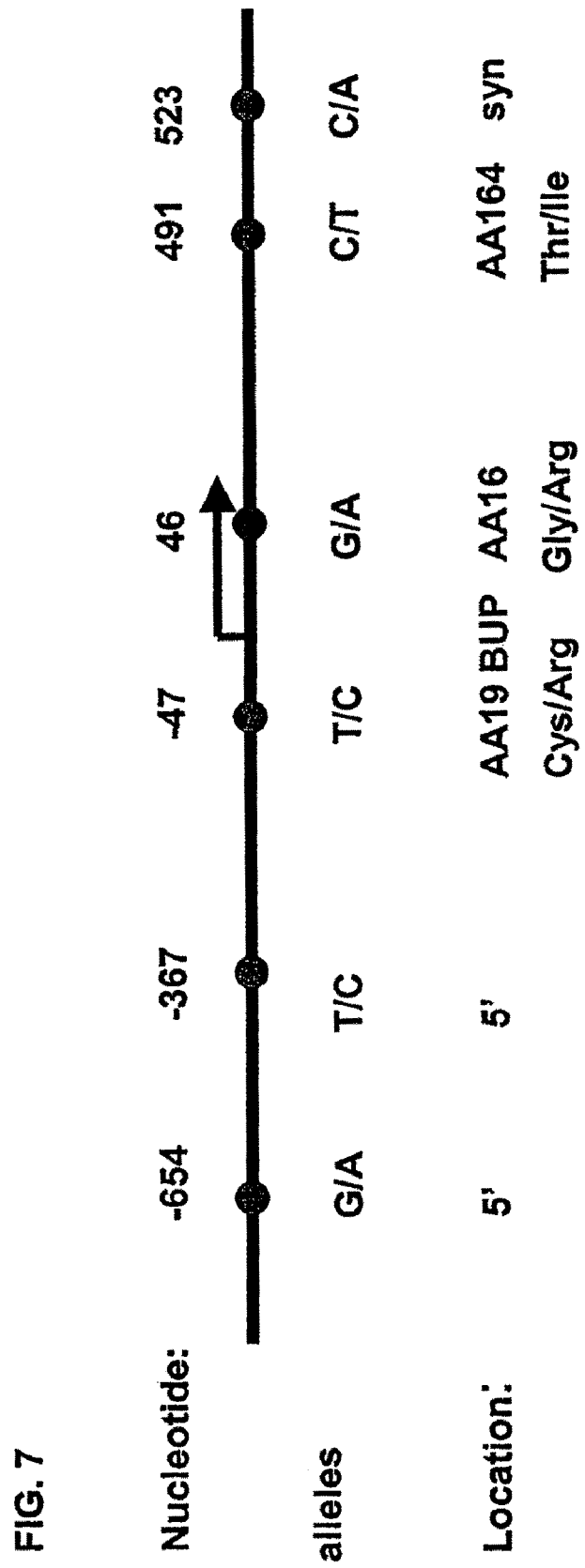

FIG. 11
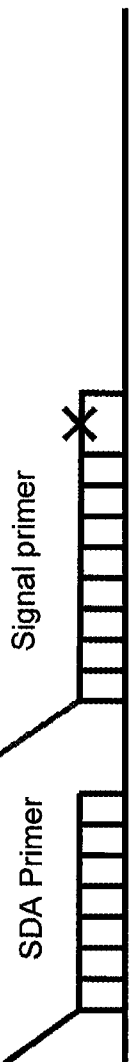
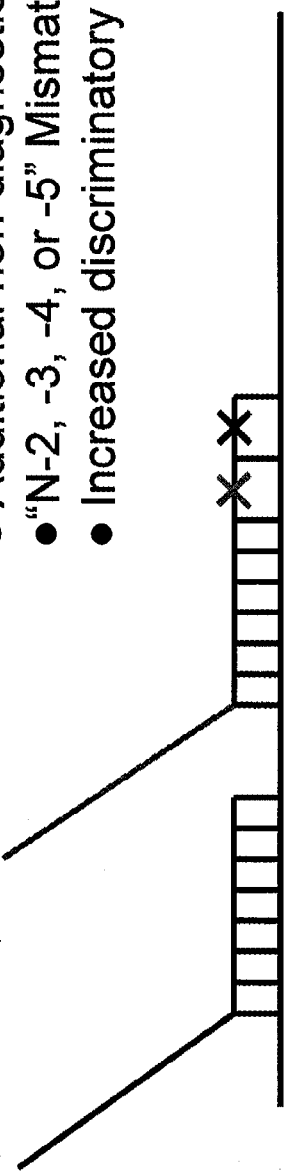

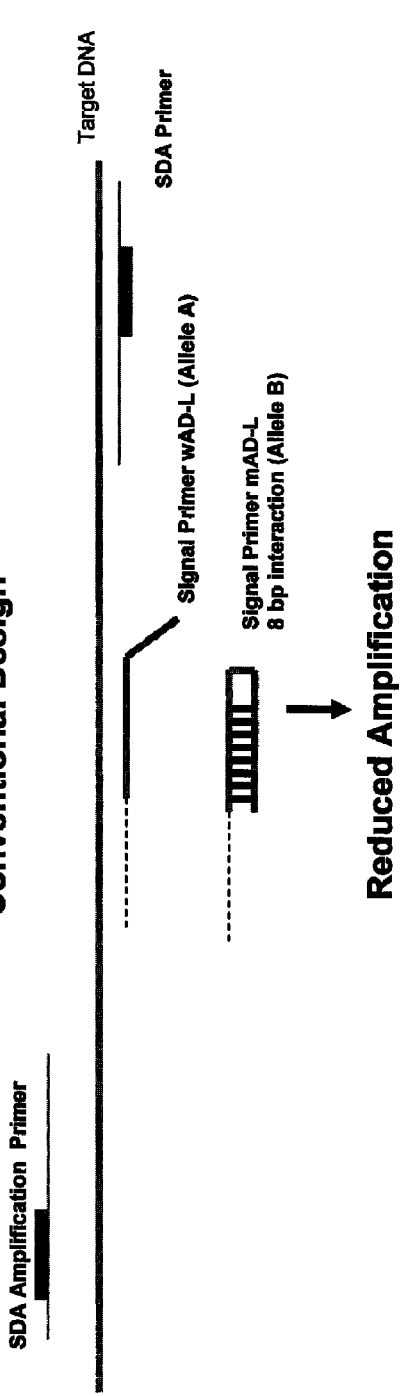
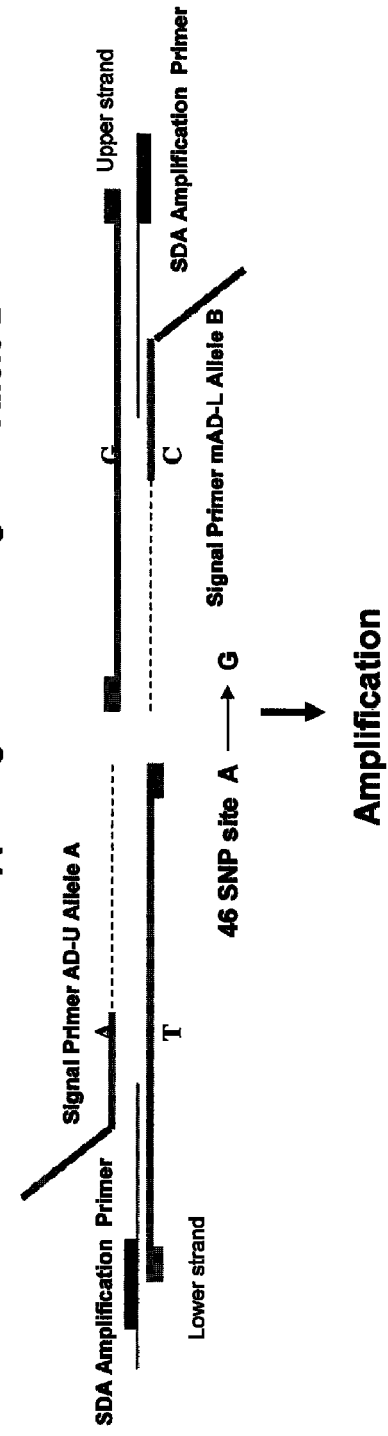
FIG. 12A

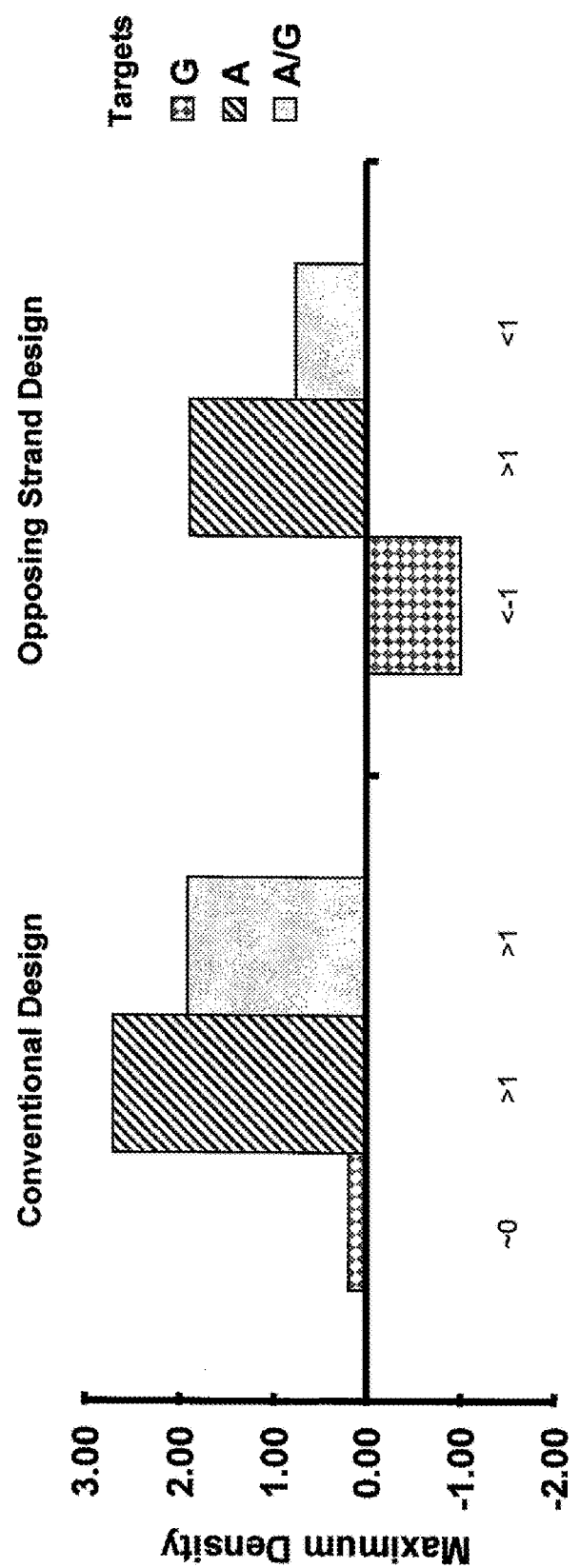

SEQUENCE LISTING

```
<160> NUMBER OF SEQ ID NOS: 56

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Synthetic
      signal primer

<400> SEQUENCE: 1
ccaaaatgac agcttctgat ggaatgactc actgagttgg aacgt            45

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      reporter probe

<400> SEQUENCE: 2
tacctcgagt gcagccaaaa gacagcttct gatggaa                     37

<210> SEQ ID NO 3
<211> LENGTH: 48
<212> TYPE: DNA
<213> ORGANISM: Human immunodeficiency virus

<400> SEQUENCE: 3
gaaagacgtt agccaccata cggataccccc ttttcttta aaattgtg          48

<210> SEQ ID NO 4
<211> LENGTH: 52
<212> TYPE: DNA
<213> ORGANISM: Human immunodeficiency virus
```

-continued

<400> SEQUENCE: 4
gaaagacgtt agccaccata cggatacccc ttttctttta aaattgtgga tg         52

<210> SEQ ID NO 5
<211> LENGTH: 45
<212> TYPE: DNA
<213> ORGANISM: Human immunodeficiency virus

<400> SEQUENCE: 5
gaaagacgtt agccaccata cggatacccc ttttctttta aaatt                 45

<210> SEQ ID NO 6
<211> LENGTH: 46
<212> TYPE: DNA
<213> ORGANISM: Human immunodeficiency virus

<400> SEQUENCE: 6
gaaagacgtt agccaccata cggatacccc ttttctttta aaattg                46

<210> SEQ ID NO 7
<211> LENGTH: 43
<212> TYPE: DNA
<213> ORGANISM: Human immunodeficiency virus

<400> SEQUENCE: 7
acgttagcca ccatacggat acccctttc ttttaaaatt gtg                    43

<210> SEQ ID NO 8
<211> LENGTH: 47
<212> TYPE: DNA
<213> ORGANISM: Human immunodeficiency virus

<400> SEQUENCE: 8
acgttagcca ccatacggat acccctttc ttttaaaatt gtggatg                47

<210> SEQ ID NO 9
<211> LENGTH: 40
<212> TYPE: DNA
<213> ORGANISM: Human immunodeficiency virus

<400> SEQUENCE: 9
acgttagcca ccatacggat acccctttc ttttaaaatt                        40

<210> SEQ ID NO 10
<211> LENGTH: 41
<212> TYPE: DNA
<213> ORGANISM: Human immunodeficiency virus

<400> SEQUENCE: 10
acgttagcca ccatacggat acccctttc ttttaaaatt g                      41

<210> SEQ ID NO 11
<211> LENGTH: 38
<212> TYPE: DNA
<213> ORGANISM: Human immunodeficiency virus

<400> SEQUENCE: 11
agccaccata cggatacccc ttttctttta aaattgtg                         38

<210> SEQ ID NO 12
<211> LENGTH: 42
<212> TYPE: DNA
<213> ORGANISM: Human immunodeficiency virus

<400> SEQUENCE: 12
agccaccata cggatacccc ttttcttttta aaattgtgga tg 42

<210> SEQ ID NO 13
<211> LENGTH: 35
<212> TYPE: DNA
<213> ORGANISM: Human immunodeficiency virus

<400> SEQUENCE: 13
agccaccata cggatacccc ttttcttttta aaatt 35

<210> SEQ ID NO 14
<211> LENGTH: 36
<212> TYPE: DNA
<213> ORGANISM: Human immunodeficiency virus

<400> SEQUENCE: 14
agccaccata cggatacccc ttttcttttta aaattg 36

<210> SEQ ID NO 15
<211> LENGTH: 34
<212> TYPE: DNA
<213> ORGANISM: Human immunodeficiency virus

<400> SEQUENCE: 15
tgcccgagtg aaagacgtta gccaccatac ggat 34

<210> SEQ ID NO 16
<211> LENGTH: 40
<212> TYPE: DNA
<213> ORGANISM: Human immunodeficiency virus

<400> SEQUENCE: 16
tagtgcccga gcactgaaag acgttagcca ccatacggat 40

<210> SEQ ID NO 17
<211> LENGTH: 35
<212> TYPE: DNA
<213> ORGANISM: Human immunodeficiency virus

<400> SEQUENCE: 17
tagtgcccga gcactacgtt agccaccata cggat 35

<210> SEQ ID NO 18
<211> LENGTH: 30
<212> TYPE: DNA
<213> ORGANISM: Human immunodeficiency virus

<400> SEQUENCE: 18
tagtgcccga gcactagcca ccatacggat 30

<210> SEQ ID NO 19
<211> LENGTH: 40
<212> TYPE: DNA
<213> ORGANISM: Human immunodeficiency virus

<400> SEQUENCE: 19
tagtgctcgg gcactgaaag acgttagcca ccatacggat 40

<210> SEQ ID NO 20
<211> LENGTH: 43
<212> TYPE: DNA
<213> ORGANISM: Human immunodeficiency virus

```
<400> SEQUENCE: 20
ggttggctcg aggttggtga aagacgttag ccaccatacg gat                 43

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acgttagcca ccatacggat cctccttctc ctggg                          35

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgattccgct ccagacttct cgggctcgcc ctccttct                       38

<210> SEQ ID NO 23
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agtgtgcatg tcggtga                                              17

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaggcacgca catacag                                              17

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
accgcatcga atgactgtct cgggtgtgtc tcagtgtct                      39

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
```

```
cgattccgct ccagtcttct cgggatacac cctggcag                            38
```

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
acgttagcca ccatacggat tgtggttcgg tataagtatg a                        41
```

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
agctatccgc cataagccat tgtggttcgg tataagtgta a                        41
```

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
tccagggagc agttg                                                     15
```

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
aactttcggc caatg                                                     15
```

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
cgattccgct ccagacttct cgggcgaccg ggccagc                             37
```

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
agctatccgc cataagccat ccctccttct cctgag                              36
```

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acagccgctg aatgag                                                    16

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tggcaggtaa gcgcact                                                   17

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgattccgct ccagacttct cgggtccgca gagcc                               35

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
accgcatcga atgactgtct cgggagcgcc tcag                                34

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acgttagcca ccatacggat tccgtgggtc cgcccg                              36

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agctatccgc cataagccat ccgtgggtcc gcctg                               35

```
<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tggggcaatc cgggaa                                                    16

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cacacctcgt cccctt                                                    16

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgattccgct ccagacttct cgggtggcag cgccttctt                           39

<210> SEQ ID NO 42
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
accgcatcga atgactgtct cggggtggtc cggcgcat                            38

<210> SEQ ID NO 43
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
acgttagcca ccatacggat cttgctggca cccaaaag                            38

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agctatccgc cataagccat cttgctggca cccaaagg                            38

<210> SEQ ID NO 45
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aataaggcac gggtg                                                    15

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ttggttcgtg aagaagt                                                  17

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgattccgct ccagacttct cgggtggtgt ggattgtgtc                         40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
accgcatcga atgactgtct cgggtctcat tggcatagca                         40

<210> SEQ ID NO 49
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acgttagcca ccatacggat aatgggcaag aaggaggt                           38

<210> SEQ ID NO 50
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agctatccgc cataagccat aatgggcaag aaggagat                           38

<210> SEQ ID NO 51
<211> LENGTH: 38
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 51
agctatccgc cataagccat acagatgcac tagtaccg                              38

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agctatccgc cataagccat acagatgcac tagtacag                              38

<210> SEQ ID NO 53
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
tagcgcccga gcgctacgtt agccaccata cggat                                 35

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
agttgccccg aggcaactag ctatccgcca taagccat                              38

<210> SEQ ID NO 55
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acgttagcca ccatacggat tgtggttcgg tataagtctg a                          41

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agctatccgc cataagccat tgtggttcgg tataagtcta a                          41
```

METHODS FOR DETECTING NUCLEIC ACID SEQUENCE VARIATIONS

CROSS-REFERENCE TO RELATED APPLICATIONS

This application is a continuation of U.S. Ser. No. 11/724,180, filed on Mar. 15, 2007, now abandoned, which is a continuation of U.S. Ser. No. 10/202,896, filed on Jul. 26, 2002, now abandoned, which is a continuation-in-part of U.S. Ser. No. 09/335,218, filed on Jun. 17, 1999, now abandoned, and is a continuation-in-part of U.S. Ser. No. 09/894,788 filed on Jun. 28, 2001 (now U.S. Pat. No. 6,656,680, issued on Dec. 3, 2003), which is a divisional of U.S. Ser. No. 09/590,061, filed on Jun. 8, 2000 (now U.S. Pat. No. 6,316,200, issued on Nov. 13, 2001), the entire contents of which are incorporated by reference herein.

FIELD OF THE INVENTION

The present invention relates to oligonucleotides and methods for amplifying and detecting sequence variations in target nucleic acids such as the human $\beta_2$-adrenergic receptor ($\beta_2$AR) gene. The preferred method involves using fluorescent real-time thermophilic Strand Displacement Amplification (SDA) with nucleic acid primers and adapter-mediated universal detector probes to amplify and detect allele-specific sequences from blood, tissue and bodily fluids.

BACKGROUND OF THE INVENTION

Sequence-specific hybridization of labeled oligonucleotide probes has long been used as a means for detecting and identifying selected nucleotide sequences, and labeling of such probes with fluorescent labels has provided a relatively sensitive, nonradioactive means for facilitating detection of probe hybridization. Recently developed detection methods employ the process of fluorescence energy transfer (FET) rather than direct detection of fluorescence intensity for detection of probe hybridization. Fluorescence energy transfer occurs between a donor fluorophore and a quencher dye (which may or may not be a fluorophore) when the absorption spectrum of one (the quencher) overlaps the emission spectrum of the other (the donor) and the two dyes are in close proximity. Dyes with these properties are referred to as donor/quencher dye pairs or energy transfer dye pairs. The excited-state energy of the donor fluorophore is transferred by a resonance dipole-induced dipole interaction to the neighboring quencher. This results in quenching of donor fluorescence. In some cases, if the quencher (also referred to as an "acceptor") is also a fluorophore, the intensity of its fluorescence may be enhanced. The efficiency of energy transfer is highly dependent on the distance between the donor and quencher, and equations predicting these relationships have been developed by Förster (1948. Ann. Phys. 2, 55-75). The distance between donor and quencher dyes at which energy transfer efficiency is 50% is referred to as the Förster distance ($R_O$). Other mechanisms of fluorescence quenching are also known including, for example, charge transfer and collisional quenching. In these cases the quencher may be a fluorescent dye but it need not be. Fluorescence quenching mechanisms that are not based on FET typically do not require appreciable overlap between the absorption spectrum of the quencher and the emission spectrum of the donor fluorophore.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Typically, FET and related methods have relied upon monitoring a change in the fluorescence properties of one or both dye labels when they are brought together by the hybridization of two complementary oligonucleotides. In this format, the change in fluorescence properties may be measured as a change in the amount of energy transfer or as a change in the amount of fluorescence quenching, typically indicated as an increase in the fluorescence intensity of one of the dyes. In this way, the nucleotide sequence of interest may be detected without separation of unhybridized and hybridized oligonucleotides. The hybridization may occur between two separate complementary oligonucleotides, one of which is labeled with the donor fluorophore and one of which is labeled with the quencher. In double-stranded form there is decreased donor fluorescence (increased quenching) and/or increased energy transfer as compared to the single-stranded oligonucleotides. Several formats for FET hybridization assays are reviewed in *Nonisotopic DNA Probe Techniques* (1992. Academic Press, Inc., pgs. 311-352). Alternatively, the donor and quencher may be linked to a single oligonucleotide such that there is a detectable difference in the fluorescence properties of one or both when the oligonucleotide is unhybridized vs. when it is hybridized to its complementary sequence. In this format, donor fluorescence is typically increased and energy transfer/quenching are decreased when the oligonucleotide is hybridized. For example, an oligonucleotide labeled with donor and quencher dyes may contain self-complementary sequences that base-pair to form a hairpin which brings the two dyes into close spatial proximity where energy transfer and quenching can occur. Hybridization of this oligonucleotide to its complementary sequence in a second oligonucleotide disrupts the hairpin and increases the distance between the two dyes, thus reducing quenching. See Tyagi and Kramer (1996. *Nature Biotech.* 14, 303-308) and B. Bagwell, et al. (1994. *Nucl. Acids Res.* 22, 2424-2425; U.S. Pat. No. 5,607,834). Homogeneous methods employing energy transfer or other mechanisms of fluorescence quenching for detection of nucleic acid amplification have also been described. L. G. Lee, et al. (1993. *Nuc. Acids Res.* 21, 3761-3766) disclose a real-time detection method in which a doubly-labeled detector probe is cleaved in a target amplification-specific manner during PCR. The detector probe is hybridized downstream of the amplification primer so that the 5'-3' exonuclease activity of Taq polymerase digests the detector probe, separating two fluorescent dyes which form an energy transfer pair. Fluorescence intensity increases as the probe is cleaved.

Signal primers (sometimes also referred to as detector probes) which hybridize to the target sequence downstream of the hybridization site of the amplification primers have been described for homogeneous detection of nucleic acid amplification (U.S. Pat. No. 5,547,861 which is incorporated herein by reference). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. Examples of homogeneous detection methods for use with single-stranded signal primers are described in U.S. Pat. No. 5,550,025 (incorporation of lipophilic dyes and restriction sites) and U.S.

Pat. No. 5,593,867 (fluorescence polarization detection). More recently signal primers have been adapted for detection of nucleic acid targets using FET/fluorescence quenching methods which employ unfolding of secondary structures (e.g., U.S. Pat. No. 5,691,145 and U.S. Pat. No. 5,928,869). Partially single-stranded, partially double-stranded signal primers labeled with donor/quencher dye pairs have also recently been described. For example, U.S. Pat. No. 5,846,726 discloses signal primers with donor/quencher dye pairs flanking a single-stranded restriction endonuclease recognition site. In the presence of the target, the restriction site becomes double-stranded and cleavable by the restriction endonuclease. Cleavage separates the dye pair and decreases donor quenching. U.S. Pat. No. 6,130,047 (incorporated herein by reference) describes a detector nucleic acid comprised of two complementary oligonucleotides that are hybridized to form a duplex. One of the oligonucleotides is longer than the other and contains a single-stranded tail sequence capable of binding target sequences. The two oligonucleotides also comprise a fluorophore/quencher dye pair such that when the two oligonucleotides are hybridized to each other fluorescence remains substantially quenched, because fluorophore and quencher remain in close spatial proximity. Hybridization of a target sequence to the single-stranded tail of the longer oligonucleotide enables a polymerase-mediated displacement of the shorter oligonucleotide from the longer one, resulting in separation of quencher from fluorophore and a corresponding increase in fluorescence of the sample.

U.S. Pat. No. 6,379,888 (incorporated herein by reference) also discloses a signal primer comprised of two complementary oligonucleotides that are hybridized to form a duplex with one of the oligonucleotides containing in addition a single-stranded tail capable of binding target sequences. In this case, however, the shorter of the two oligonucleotides contains both a fluorophore and a quencher which are held spatially apart when the shorter oligonucleotide is hybridized to the longer, unlabeled oligonucleotide. Hybridization of a target sequence to the single-stranded tail of the longer oligonucleotide triggers a polymerase-mediated displacement of the shorter oligonucleotide. Upon displacement, the shorter oligonucleotide adopts a conformation that brings the fluorophore and quencher into close proximity so fluorescence decreases in the presence of target. U.S. Pat. No. 5,866,336 describes use of a fluorescently labeled hairpin on an amplification primer in PCR. The 3' end of the hairpin primer hybridizes to the complement of a non-target sequence appended to the target by a second primer. In this system, the hairpin primer plays an integral part in amplification of the target sequence and must be extendible. In contrast, in the present invention it is not necessary for the reporter probe to be extendible, as it does not participate in amplification of the target sequence but generates signal in a separate series of reaction steps which occur concurrently with target amplification. In further contrast, the signal primers of the invention hybridize to an internal sequence of the target (i.e., between the amplification primers), so that the signal generation reaction detects a subsequence of the target, not the amplification product itself.

Detecting and identifying variations in DNA sequences among individuals and species has provided insights into evolutionary relationships, inherited disorders, acquired disorders and other aspects of molecular genetics including predisposition to infectious or non-infectious disease and prediction of therapeutic efficacy. Analysis of sequence variation has routinely been performed by analysis of restriction fragment length polymorphism (RFLP) which relies on a change in restriction fragment length as a result of a change in sequence. RFLP analysis requires size-separation of restriction fragments on a gel and Southern blotting with an appropriate probe. This technique is slow and labor intensive and cannot be used if the sequence change does not result in a new or eliminated restriction site.

More recently, PCR has been used to facilitate sequence analysis of DNA. For example, allele-specific oligonucleotides have been used to probe dot blots of PCR products for disease diagnosis. If a point mutation creates or eliminates a restriction site, cleavage of PCR products may be used for genetic diagnosis (e.g., sickle cell anemia). General PCR techniques for analysis of sequence variations have also been reported. S. Kwok, et al. (1990. Nucl. Acids Res. 18:999-1005) evaluated the effect on PCR of various primer-template mismatches for the purpose of designing primers for amplification of HIV which would be tolerant of sequence variations. The authors also recognized that their studies could facilitate development of primers for allele-specific amplification. Kwok, et al. report that a 3' terminal mismatch on the PCR primer produced variable results. In contrast, with the exception of a 3' T mismatch, a 3' terminal mismatch accompanied by a second mismatch within the last four nucleotides of the primer generally produced a dramatic reduction in amplification product. The authors report that a single mismatch one nucleotide from the 3' terminus (N-1), two nucleotides from the 3' terminus (N-2) or three nucleotides from the 3' terminus (N-3) had no effect on the efficiency of amplification by PCR. C. R. Newton, et al. (1989. Nucl. Acids Res. 17:2503-2516) report an improvement in PCR for analysis of any known mutation in genomic DNA. The system is referred to as Amplification Refractory Mutation System or ARMS and employs an allele-specific PCR primer. The 3' terminal nucleotide of the PCR amplification primer is allele specific and therefore will not function as an amplification primer in PCR if it is mismatched to the target. The authors also report that in some cases additional mismatches near the 3' terminus of the amplification primer improve allele discrimination.

SUMMARY OF THE INVENTION

The present invention provides methods for identifying sequence variations in a nucleic acid sequence of interest using an unlabeled signal primer comprising a 5' adapter sequence to mediate detection by generic or universal labeled reporter probes. The method is based upon the universal detection system described in U.S. Pat. No. 6,316,200 (herein incorporated by reference) (FIG. 1A, B). The 3' end of the reporter probe hybridizes to the complement of the 5' adapter sequence to produce a 5' overhang. Polymerase is used to fill in the overhang and synthesize the compliment of the 5' overhang of the reporter probe. Synthesis of the reporter probe compliment is detected, directly or indirectly, as an indication of the presence of the specific target allele.

The 5' tail sequence of the signal primer comprises a sequence which does not hybridize to the target (the adapter sequence). The adapter sequence may be selected such that it is the same in a variety of signal primers which have different 3' target binding sequences (i.e., a "universal" 5' tail sequence). This allows a single reporter probe sequence to be used for detection of any desired target sequence, which is an advantage in that synthesis of the reporter probe is more complex due to the labeling. Further, the invention simplifies the synthesis of the target-specific signal primer. As the signal primer is not labeled, signal primers with different target binding sequences specific for different targets may be more easily and efficiently synthesized. The methods of the invention therefore permit the detection of many different mutations using a single pair of detectable reporter probes and this offers a particular advantage over other systems that use target-specific reporter probes for the detection of allelic variations. The present invention offers significant benefits over such techniques in terms of cost and speed of development of novel assays.

The methods of the invention are particularly well suited, but are not limited to, the detection and identification of single nucleotide differences between the target sequence being evaluated (e.g., a mutant allele of a gene) and a second nucleic acid sequence (e.g., a wild-type allele for the same gene), as they make use of nucleotide mismatches near the 3' end of the signal primer to discriminate between a first nucleotide and a second nucleotide at the site of interest in the target. Both the wild-type and mutant alleles can be detected in the same reaction by incorporating signal primers specific for each target (FIG. 2A, B). In a preferred embodiment, the diagnostic nucleotide (SNP-site) is located one base (N-1) from the 3' terminus of the signal primer. This reduces the efficiency of non-specific polymerase extension by reducing the stability of base pairing and base stacking interactions at the 3' end of the signal primer. A further embodiment of the invention involves the creation of artificial mismatches in the signal primer sequence at one or more nucleotides (e.g., N-2, N-3, N-4, and N-5) near the SNP-site (N-1). This further reduces the stability of hybridization at the 3' end of the signal primer and lowers the melting temperature of the primer:target hybrid. This embodiment has no impact on the amplification efficiency of the target nucleic acid as this occurs independently of hybridization of the signal primer. However, the efficiency of detection, particularly that of a target sequence containing multiple mismatches with the signal primer is diminished, thereby enhancing allelic discrimination. This may be of particular importance in systems designed to discriminate sequence variations located in G-C rich regions of DNA and in which base pairing and base stacking interactions are very strong. Such mismatches may also be introduced in the signal primer downstream of the diagnostic nucleotide (e.g., at positions $\delta+1$, $\delta+2$, $\delta+3$ or $\delta+4$ relative to the diagnostic nucleotide, $\delta$) to bring about a similar reduction in the efficiency of polymerase extension. The disclosed methods have distinct advantages over other primer extension-based systems for allelic discrimination in which the diagnostic nucleotide is incorporated in an amplification primer. In the method of the present invention, multiple mutations can be detected within the target sequence using the same amplification primers in conjunction with unlabeled signal primers that are specific for each mutation. This obviates the need to design and optimize multiple amplification systems for the detection of each individual mutation.

In a preferred embodiment, the method of the invention employs Strand Displacement Amplification (SDA) as the means of target amplification. SDA relies upon the coordinated activity of a DNA polymerase and restriction enzyme to amplify target nucleic acid. A limitation of SDA therefore, is that the target sequence ideally should not contain the SDA restriction enzyme recognition site. For many applications, this limitation can be overcome through careful selection of the target region. However, for SNP analysis in which a specific mutation at a particular site must be identified, it is not always possible to avoid undesirable restriction sites. To overcome this obstacle, artificially created mismatches in bumper and amplification primer sequences can be used to protect the amplicon from the digestion by the restriction enzyme used in SDA (FIGS. 3A and B).

In the isothermal amplification methods of the present invention a mismatch on the detector/amplification primer at N-1 to N-4 and a complementary 3' terminal nucleotide results in excellent allele discrimination, particularly if an optional second nondiagnostic mismatch is included. This embodiment is therefore preferred for detector/amplification primers of the invention.

In an alternative preferred embodiment, the detector primer is used in an isothermal amplification reaction as a signal primer (also referred to as a detector probe) as taught in U.S. Pat. No. 5,547,861, the disclosure of which is hereby incorporated by reference. In the amplification reaction, the signal primer hybridizes to the target sequence downstream of an amplification primer such that extension of the amplification primer displaces the signal primer and its extension product. After extension, the signal primer includes the downstream sequence which is the hybridization site for the second amplification primer. The second amplification primer hybridizes to the extended signal primer and primes synthesis of its complementary strand. Production of these double-stranded secondary amplification products may be detected not only as an indication of the presence of the target sequence, but in the methods of the invention a signal primer which has the sequence characteristics of a detector primer (a detector/signal primer) also facilitates detection and/or identification of SNP's within the target sequence. In this embodiment, a diagnostic mismatch at either the 3' terminus (N) or at N-1 to N-4 provides excellent allele discrimination.

Applicants hypothesize that the different results obtained with a diagnostic mismatch at the 3' terminus of a detector/signal primer as compared to a diagnostic mismatch at the 3' terminus of a detector/amplification primer may be at least partially due to a kinetic effect. If a signal primer is not efficiently extended on a target to which it is hybridized (e.g., when it contains mismatches), it will be quickly displaced from the template by extension of the upstream amplification primer. If the signal primer is efficiently extended, extension will occur before the signal primer is displaced from the target. That is, the upstream amplification primer (which is typically perfectly matched and efficiently extended) imposes a "time-limit" for extension on the detector/signal primer. In contrast, the amplification primer in an isothermal amplification reaction does not have a time-limit for extension imposed upon it by additional components of the isothermal amplification reaction or by thermocycling. Therefore, with sufficient time available, a detector/amplification primer may eventually be extended even when the extension reaction is inefficient. This phenomenon could reduce discrimination between alleles when a detector/amplification primer with a 3' terminal mismatch is employed in isothermal amplification reactions. In addition, the ability of amplification primers to correct a mismatch with the target may contribute to these observations. Amplification primers produce amplicons that are perfectly matched with the amplification primers which produced them, thus eliminating the basis of allele discrimination. In contrast, such "correction" does not occur with signal primers.

Another embodiment uses signal primers with target binding sequences that are at least partially identical to the target binding sequence of an amplification primer (FIG. 4). Competitive hybridization between two oligonucleotides in an amplification/detection system has been described previously (U.S. Pat. No. 6,258,546 herein incorporated by reference) for qualitative and quantitative detection of nucleic acids. This approach provides detection efficiency that is equal to or better than that of conventional signal primers that lie entirely between the amplification primers, while still maintaining the specificity derived from use of an internal probe. Overlap between the hybridization regions of the amplification and signal primers allows for flexibility in assay design and a reduction in overall amplicon length, with the resulting potential for enhanced amplification efficiency. This is important because flexibility in system design is necessary to avoid primer:primer interactions, restriction enzyme recognition sites, amplicon secondary structure and regions of excessively high G-C content. Overlap of the signal primer and an amplification primer may also enhance allelic discrimination by providing competition between closely related sequences for hybridization to the target sequence. In such a system containing two signal primers, one specific for each of two alleles at a given locus, hybridization of the specific signal primer is thermodynamically favored but formation of this structure is the result of competition for hybridization to the target of both the amplification primer and the mismatched signal primer.

An advantage of the preferred embodiments of the disclosed methods is the ability to detect sequence variations in a broad range of clinical samples without the need for extensive sample processing. The disclosed methods for detection of SNPs using specific signal primers in conjunction with SDA offer the ability to perform genotyping with a variety of sample types including blood, urine and buccal swabs without prior purification of nucleic acid. The lack of a significant sample processing required greatly reduces cost and provides improved turnaround time for results.

The signal primer adapter-mediated universal detection system of the invention provides a simple, rapid, sensitive and specific method for SNP analysis, haplotyping and detection of other nucleotide acid sequence variations. The most preferred embodiment of the invention involves homogeneous real-time genotyping of a sample including forensic samples such as blood, tissue and body fluid samples using SDA with minimal sample processing. The present invention is a powerful tool for genotyping in clinical diagnostics, forensics and drug discovery with or without nucleic acid sample preparation.

DESCRIPTION OF THE DRAWINGS

FIGS. 2A and 2B illustrate detection of sequence variations according to the method of the invention.

FIGS. 3A and 3B illustrate protection of target sequences from digestion by the restriction enzyme(s) involved in strand displacement amplification.

FIG. 4 illustrates use of overlapping amplification and signal primers (SEQ ID NOs: 21 and 22, as utilized in Example 8) for detection of sequence variations.

FIG. 7 illustrates the positions of six key β2AR SNPs involved in haplotype analysis.

FIG. 11 illustrates the introduction in Example 9 of additional mismatches in the signal primer to enhance allelic discrimination.

FIG. 12A illustrates the use in Example 11 of opposing signal primers directed towards opposite strands of the target sequence for detection of the +46 β2AR SNP.

FIG. 12B illustrates the results obtained in Example 11 using the opposing signal primer configuration in the +46 β2AR assay system.

DETAILED DESCRIPTION OF THE INVENTION

Figure 1A:
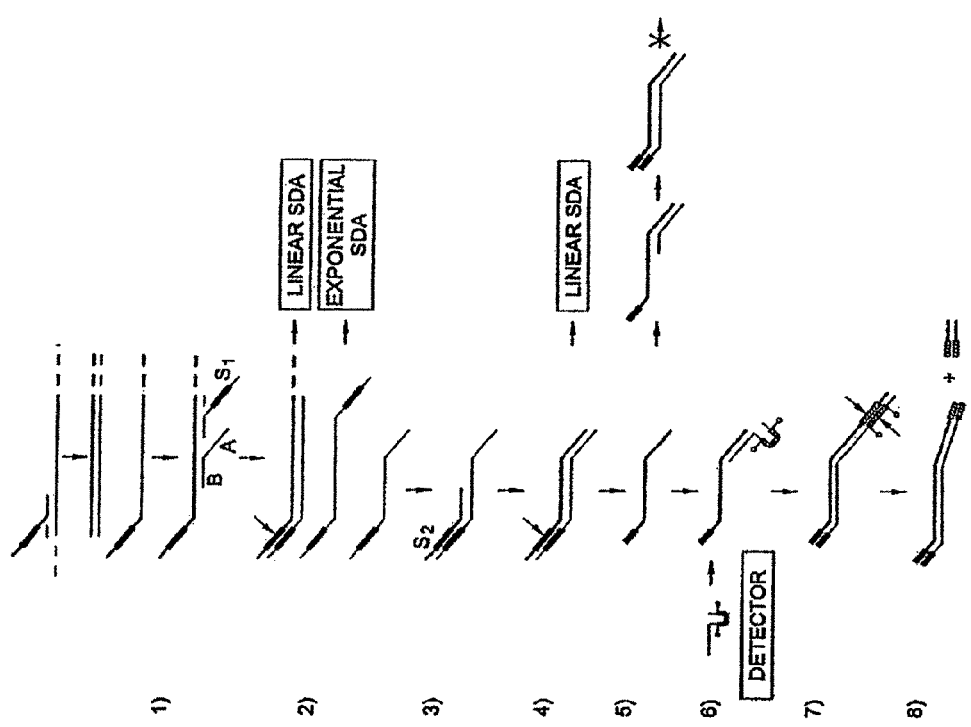
FIG. 1A illustrates detection of a nucleic acid target sequence in a Strand Displacement Amplification (SDA) reaction according to the method of the invention.

Certain terms used herein are defined as follows:

An "amplification primer" is a primer for amplification of a target sequence by primer extension. For SDA, the 3' end of the amplification primer (the target binding sequence) hybridizes at the 3' end of the target sequence. The amplification primer comprises a recognition site for a restriction endonuclease near its 5' end. The recognition site is for a restriction endonuclease which will cleave one strand of a DNA duplex when the recognition site is hemimodified ("nicking"), as described in U.S. Pat. No. 5,455,166; U.S. Pat. No. 5,270,184 and EP 0 684 315. As no special sequences or structures are required to drive the amplification reaction, amplification primers for PCR may consist only of target binding sequences. Amplification primers for 3SR and NASBA, in contrast comprise an RNA polymerase promoter near the 5' end. The promoter is appended to the target sequence and serves to drive the amplification reaction by directing transcription of multiple RNA copies of the target.

"Extension products" are nucleic acids which comprise a primer or a portion of a primer and a newly synthesized strand which is the complement of the sequence downstream of the primer binding site. Extension products result from hybridization of a primer to a template containing a complementary sequence and extension of the primer by polymerase using the template.

The terms "target" or "target sequence" refer to nucleic acid sequences to be amplified or detected. These include the original nucleic acid sequence to be amplified, its complementary second strand and either strand of a copy of the original sequence which is produced by replication or amplification. A target sequence may also be referred to as a template for extension of hybridized primers.

A "signal primer" according to the present invention comprises a 3' target binding sequence which hybridizes to a complementary sequence in the target and further comprises a 5' tail sequence which is not complementary to the target (the adapter sequence). The adapter sequence is selected such that its complementary sequence will hybridize to the 3' end of the reporter probe described below. In some embodiments of the invention the adapter sequence is selected such that its complementary sequence binds to both the 3' end of the reporter probe and to a sequence within the reporter moiety of the reporter probe, as described below. In preferred embodiments of the invention, the signal primer does not comprise a detectable label.

A "diagnostic nucleotide" of the present invention is a nucleotide of the signal primer that forms a Watson-Crick complementary base pair, when signal primer and target sequence are hybridized, with the polymorphic or variant nucleotide of interest in the target sequence. The diagnostic nucleotide permits different alleles, SNPs or sequence variants to be distinguished from each other because the diagnostic nucleotide will only participate in a Watson-Crick base pair if the signal primer is hybridized to the correct target allele, SNP or sequence variant. Hybridization of the signal primer to an incorrect allele, SNP or sequence variant will cause the diagnostic nucleotide to form a mismatch, rather than a base-pair, with the variant nucleotide of the incorrect target. For example, if the correct target allele contains the base G at the variant nucleotide site, then the signal primer for this allele will contain base C as the diagnostic nucleotide, such that hybridization of the signal primer with correct target allele will form a C:G base pair between the diagnostic nucleotide of the signal primer and the variant nucleotide of the target. Hybridization of this signal primer with an incorrect allele containing, for example, base A as the variant nucleotide would create an C:A mismatch between the diagnostic nucleotide and incorrect target. Efficient extension of the signal primer will occur only if the diagnostic nucleotide participates in a Watson-Crick base pair when the signal primer is hybridized to a potential target sequence. If the diagnostic nucleotide participates in a mismatch rather than a proper Watson-Crick pair, extension of the signal primer will be retarded.

A "reporter probe" according to the present invention comprises a label which is preferably at least one donor/quencher dye pair, i.e., a fluorescent donor dye and a quencher for the donor fluorophore. The label is linked to a sequence or structure in the reporter probe (the reporter moiety) which does not hybridize directly to the target sequence. The sequence of the reporter probe 3' to the reporter moiety is selected to hybridize to the complement of the signal primer adapter sequence. In general, the 3' end of the reporter probe does not contain sequences with any significant complementarity to the target sequence. In some instances, however, the reporter probe may contain the sequence that hybridizes to the adapter complement and another short sequence at the 3' end that hybridizes to a short segment of the target complement. In this case, the region of target complementarity is not large enough to permit significant hybridization without concurrent hybridization of the adapter-specific region of the reporter probe. The label of the reporter probe is detected as an indication of the presence of a complement of the reporter moiety which renders it double-stranded, thereby indicating the presence of or the amplification of the target. The 3' terminus of the reporter probe may be capped to prevent extension by polymerase or it may be extendible. Capping may enhance performance by reducing background signal and the nonproductive consumption of reagents in spurious side-reactions resulting from the formation of primer dimers and other errant priming events.

Any nucleic acid sequence or structure which can be labeled such that the presence of its complement, generated according to the methods of the invention, indicates the presence of the target sequence can serve as the reporter moiety of the reporter probe. Preferably, the reporter moiety is labeled with a donor/quencher dye pair such that donor fluorescence is quenched prior to detection of a target and such that quenching of donor fluorescence is reduced as an indication of the presence of the target. The reporter moiety may be a secondary structure at the 5' end of the reporter probe, such as a stem-loop (or hairpin) as described in U.S. Pat. No. 5,928, 869 or a G-quartet as described in U.S. Pat. No. 5,691,145. The secondary structure is labeled such that the donor and quencher are in close proximity when the secondary structure is folded, resulting in quenching of donor fluorescence. In the presence of target, the secondary structure is unfolded in a target-dependent primer extension reaction so that the distance between the donor and quencher is increased. This decreases quenching and produces an increase in donor fluorescence which can be detected as an indication of the presence of the target sequence. Alternatively, the reporter moiety may be a single-stranded sequence at the 5' end of the reporter probe which is labeled with the donor and quencher in sufficiently close proximity to produce quenching and which contains a single-stranded restriction endonuclease recognition site (RERS) as described in U.S. Pat. No. 5,846,726 and U.S. Pat. No. 5,919,630. In the single-stranded reporter probe, the RERS is not cleavable. However, in the presence of target, the single-stranded RERS is converted to double-stranded form in a target-dependent primer extension reaction and thereby becomes cleavable. Treatment with the appropriate restriction endonuclease cleaves the RERS between the two dyes, separating them into separate nucleic acid fragments. The associated increase in distance between the dyes results in reduced quenching of donor fluorescence which can be detected as an indication of the presence of the target sequence. In a further embodiment, an RERS reporter moiety may be rendered nickable in the target-dependent primer extension reaction, as taught in U.S. Pat. No. 5,846,726 and U.S. Pat. No. 5,919,630. In this embodiment, when the RERS is rendered double-stranded the restriction endonuclease nicks the strand to which the donor and quencher are linked. Polymerase extends from the nick, displacing from the reporter probe a single-stranded fragment linked to one of the dyes. This also increases the distance between the donor and quencher and results in an increase in donor fluorescence due to decreased quenching. A reporter moiety may also be a double stranded sequence at the 5' end of the reporter probe as disclosed by U.S. Pat. No. 6,130,047. In this case, fluorophore and quencher reside on different oligonucleotides, comprising the 5' end of the reporter probe, and are held in close spatial proximity by hybridization of the two oligonucleotides. Hybridization of target to the 3' end of the reporter probe triggers polymerase-mediated separation of the two oligonucleotides and separation of quencher from fluorophore, resulting in increased fluorescence. U.S. Pat. No. 6,379,888 describes another double-stranded reporter moiety at the 5' end of the reporter probe. In this case, fluorophore and quencher reside on the same oligonucleotide but are held apart when this oligonucleotide hybridizes to the complementary oligonucleotide comprising the second oligonucleotide of the reporter probe. The second oligonucleotide is unlabeled, longer than the labeled oligonucleotide, and also contains a single-stranded sequence comprising the 3' end of the reporter probe. Hybridization of the target to the 3' end triggers polymerase-mediated displacement of the shorter, labeled oligonucleotide which then folds into a conformation that brings quencher and fluorophore into close spatial proximity, decreasing fluorescence. In this case, the presence of target is thus indicated by reduced fluorescence of the sample.

One embodiment of the method of the invention as applied to SDA is illustrated schematically in FIG. 1A. The initial steps of the reaction correspond to the signal primer reaction described in U.S. Pat. No. 5,547,861. A signal primer having a 3' target binding sequence (B) and a noncomplementary 5' tail (A) hybridizes to the target downstream from an amplification primer ($S_1$) (Step 1). As illustrated, the entire hybridization site of the signal primer is downstream from the hybridization site of the amplification primer. However, the hybridization sites of the signal primer and the amplification primer on the target may also partially overlap (typically only by several nulceotides) without significantly affecting the methods of the invention. As used herein, the term "downstream from" with respect to the hybridization sites of the signal primer and the amplification primer on the target is intended to encompass nonoverlapping and partially overlapping sites in the target. Following hybridization to the target, the amplification primer and the signal primer are simultaneously extended on the target sequence, and extension of the amplification primer displaces the single-stranded signal primer extension product (Step 2). The second amplification primer ($S_2$) hybridizes to the signal primer extension product (Step 3) and both the signal primer extension product and the amplification primer are extended to produce a double-stranded secondary amplification product with a hemimodified RERS at one end (Step 4). In SDA, nicking of the unmodified $S_2$ strand of the RERS (shown as an arrow in Step 4) and displacement of the strand downstream from the nick produces a single-stranded oligonucleotide which comprises the complement of the signal primer (Step 5). The complement of the signal primer and the double-stranded secondary amplification product are produced only when the target is present and amplified. They may therefore be detected as an indication of target amplification.

In the detection method taught in U.S. Pat. No. 5,547,861, the double-stranded secondary amplification product is detected. In contrast, the present invention detects the single-stranded oligonucleotide which is displaced from the double-stranded secondary amplification product after nicking. As this oligonucleotide comprises the complement of the signal primer, the 3' end of the reporter probe hybridizes to it (Step 6). The 5' end of the reporter probe, containing the labeled structure or sequence, forms an overhang with two recessed 3' ends which are appropriate substrates for polymerase. If the reporter probe is not capped to prevent extension, both the reporter probe and the single-stranded oligonucleotide are extended to produce a completely double-stranded molecule (Step 7). If the reporter probe is not extendible, only the recessed 3' end of the single-stranded oligonucleotide (which comprises the complement of the signal primer) is extended and the product is partially single-stranded and partially double-stranded. In either case, the sequence complementary to the labeled structure or sequence of the reporter probe is synthesized, rendering it double-stranded. FIG. 1A exemplifies the invention using a hairpin reporter moiety labeled with a donor/quencher dye pair such that donor fluorescence is quenched. It will be appreciated from this example that it may not be necessary for the reporter moiety to be rendered entirely double-stranded to be detected. For example, a partial complement of the hairpin structure can be sufficient to keep the arms of the stem from hybridizing to each other. As used herein, "double-stranded reporter moiety" is intended to encompass both fully and partially double-stranded reporter moieties provided they are sufficiently double-stranded to render the reporter moiety detectable. When the reporter moiety is rendered double-stranded in the primer extension reaction, the hairpin is unfolded. Upon unfolding, the two dyes become sufficiently spatially separated to reduce or eliminate quenching of donor fluorescence by the quencher. The resulting increase in donor fluorescence, or a change in another fluorescence parameter associated with a change in fluorescence quenching (such as fluorescence lifetime, fluorescence polarization or a change in emission of the quencher/acceptor dye), may be detected as an indication of amplification of the target sequence. In addition, as illustrated in FIG. 1A, multiple reporter moieties may be combined in a single reporter probe, for example a labeled hairpin may comprise a single-stranded RERS in the single-stranded "loop." In this embodiment synthesis of the complement of the reporter moiety not only unfolds the hairpin to produce an increase in fluorescence, the RERS concurrently becomes cleavable or nickable, generally producing an additional fluorescence increase.

As depicted in FIG. 1A, the folded reporter moiety (e.g., a hairpin) of the reporter probe does not hybridize to the complement of the adapter sequence. However, the adapter sequence may be selected so that its complementary sequence will hybridize to all or part of a folded reporter moiety of the reporter probe. In this case, hybridization alone will unfold or partially unfold the reporter moiety producing signal without the need for polymerase-catalyzed extension following hybridization. The folded reporter moiety in this embodiment may comprise all or part of the reporter probe sequence. In an example of such an embodiment, the reporter probe may be a molecular beacon as described by Tyagi and Kramer, supra, in which the loop of the beacon hairpin comprises all or part of the adapter sequence. As the complement of the adapter sequence is synthesized during target amplification, it binds to the molecular beacon and unfolds the structure, producing increased fluorescence. In another embodiment the reporter probe contains a single-stranded sequence 3' to the folded reporter moiety such that both the single-stranded sequence and all or part of the folded reporter moiety hybridize to the sequence complementary to the adapter sequence as it is produced during amplification.

Figure 1B:
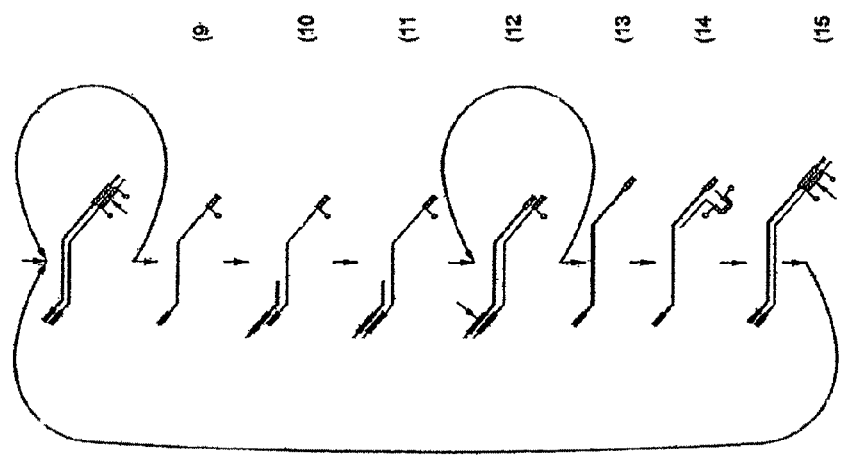
FIG. 1B illustrates the additional reaction steps which may occur when the fluorescently labeled sequence in the reporter probe is a nickable RERS.

In other alternative embodiments, other reporter moieties may be substituted in the reaction scheme shown in FIG. 1A. For example, other folded nucleic acid structures such as G-quartets may be substituted and unfolded in a similar target-dependent manner to reduce fluorescence quenching. Alternatively, a specialized linear sequence may be used as the reporter moiety, for example an RERS. When an RERS is used as the reporter moiety the donor and quencher are linked flanking the cleavage site so that when the RERS is rendered double-stranded and cleaved in a target-dependent manner the two dyes are separated onto separate nucleic acid fragments (Step 8, FIG. 1A). These alternative secondary structures may also be combined with specialized sequences, such as an RERS in a G-quartet. The RERS may alternatively be rendered nickable rather than cleavable in its double-stranded form. This is a particularly suitable embodiment for use in SDA, as incorporation of modified nucleotides and production of nickable RERS's are an integral part of the amplification reaction. Generation of a nickable RERS in the reporter probe adds some additional side reactions to the reaction scheme of FIG. 1A (shown in FIG. 1B). FIG. 1B illustrates the reaction if the RERS of the double-stranded molecule illustrated in Step 7 of FIG. 1A is nicked rather than cleaved. Referring to FIG. 1B, as polymerase extends from the nick two products are produced: the double-stranded molecule is regenerated (now carrying only one of the two dyes) and the single-stranded molecule downstream from the nick is displaced (Step 9, carrying the other of the two dyes). The double-stranded molecule can be renicked with displacement of additional single-stranded molecules and the displaced single-stranded molecules hybridize to an amplification primer (Step 10) and be extended to produce a nickable RERS in a fully double-stranded molecule (Steps 11 and 12). Further nicking and displacement produces single-stranded molecules with a partial RERS derived from the previous reporter probe at one end and no label (Step 13). This hybridizes to a new reporter probe (Step 14) and the recessed end becomes extendible as the hairpin breathes and allows the partial RERS to hybridize. Filling-in of the recessed end renders the RERS nickable (Step 15) and the displaced single-stranded molecule re-enters the reaction and the cycle repeats. This amplifies the signal initially produced from a single signal primer/target interaction by means of a separate reaction occurring independently of any further target amplification.

In yet other embodiments, double-stranded reporter moieties may be substituted in the reaction scheme shown in FIG. 1A. For example, the double-stranded reporter moieties of U.S. Pat. Nos. 6,130,047 and 6,379,888 may be substituted for the hairpin moiety depicted in FIG. 1A. In this case, the 3' tail of the reporter probe will hybridize to the complement of the adapter sequence produced in step 5 (FIG. 1A). Extension of the adapter complement sequence will then separate the shorter oligonucleotide (or oligonucleotides) of the double-stranded reporter moiety from the longer oligonucleotide, resulting in either increased or decreased fluorescence, depending on the particular mechanism described in U.S. Pat. Nos. 6,130,047 and 6,379,888.

In general, the length of the sequences involved in inter-molecular base-pairing between the complement of the adapter sequence of the signal primer and the reporter probe is not critical. For the signal primer, however, it has been observed that in general the $T_m$ of the target binding sequence has a greater influence on assay efficiency and that longer target binding sequences generally produce more fluorescent signal in the assay. This may be due to the competition between the signal primer and the extension product of the upstream amplification primer for hybridization to the target sequence. The appropriate length for the signal primer and the reporter probe is determined by the number of nucleotides required for stable base-pairing to maintain a partially double-stranded molecule under the selected reaction conditions and is within the ordinary skill in the art. For convenience, the sequences involved in base-pairing are typically between about 8 and 75 nucleotides in length. The maximum length is limited only by practical concerns such as the ease and efficiency of oligonucleotide synthesis and recovery.

Selection of the appropriate concentrations of signal primer and reporter probe in the reaction is also within the ordinary skill in the art. Preferably the concentration of signal primer and reporter probe is relatively high and the concentration of upstream amplification primer is relatively low, as this generally provides higher fluorescent signal generation in the reaction.

A second signal primer which hybridizes to the second, complementary strand of a double-stranded target sequence may optionally be included in the reaction provided that the first and second signal primers do not hybridize to each other. The second signal primer hybridizes to the second strand of the target sequence downstream of the second amplification primer and is extended and displaced by extension of the second amplification primer. The second signal primer extension product is rendered double-stranded by hybridization and extension of the first amplification primer. Generation of the double-stranded labeled structure or sequence and separation of the dye pair proceed as for the first strand of the target sequence. The second signal primer preferably comprises the same 5' adapter sequence as the first signal primer to allow detection of the products of amplification of both target strands with a single reporter probe.

In addition, multiple signal primers per strand of target may be employed if desired, each hybridizing to the target sequence downstream of the other on the same strand, with all signal primers being hybridized downstream of the amplification primer. In this manner, each signal primer is displaced by extension of the upstream detector nucleic acid and the most 5' signal primer is displaced by the amplification primer. Use of multiple signal primers has the advantage of increasing or amplifying the signal generated per target, with an increase in sensitivity of the assay. Again, it is preferable, but not necessary, that all of the signal primers comprise the same 5' adapter sequence to allow detection of all reaction products using a single reporter probe.

Multiple signal primers may also be used to simultaneously detect a plurality of different target sequences. In this case, the 5' adapter sequences of the signal primers are preferably different for each target to be detected. By labeling reporter probes specific for the 5' adapter sequence of each target-specific signal primer with donor/quencher dye pairs which are distinguishable, the presence of each target may be determined by detecting changes in the extent of fluorescence quenching in the reporter probe directed to each target. This embodiment of the invention is particularly useful for detection of single nucleotide sequence variations such as are associated with certain disease states and conditions. The target binding sequence of each signal primer may be selected to be specific for a specific sequence variant of the target. Only those signal primers which comprise the correct target binding sequence for hybridization to the target will hybridize, be extended and result in a complement of the adapter sequence being produced. The reporter probe specific for that adapter sequence complement will then produce a signal indicating which sequence variant(s) is/are present by virtue of its distinguishing label.

Alternatively, for separate assay of multiple different targets, the same 5' adapter sequence may be used in signal primers directed to the multiple different target sequences. Specificity for the different target sequences is conferred by varying the 3' target binding sequence of the signal primer. This approach not only simplifies the design and synthesis of signal primers, it allows the same reporter probe to be used to detect any desired target sequence. Commercially, this has the advantage that production of only a single reporter probe is necessary to produce assay systems for a variety of targets, thus lowering production costs and simplifying the development of assays for new targets. Further, synthesis of the various signal primers is simplified and less expensive because they do not require labeling.

The methods of the invention are useful for detecting variants of a nucleic acid sequence contained in a target nucleic acid. In particular, the methods of the invention are directed to detecting SNPs in a nucleic acid sequence of interest (e.g., alleles) and, optionally, to identifying such SNPs or alleles. Such nucleotide sequence variants may be detected directly in a sample to be analyzed during amplification of the target sequence. The inventive methods are based upon the relative inefficiency of primer extension by DNA polymerases when there are mismatches at or near the 3' end of a primer hybridized to an otherwise complementary sequence. The applicants have found that by selecting nucleotides at or near the 3' end of a signal primer such that one or more mismatches will occur when the signal primer is hybridized to a first allele of a target nucleic acid and correct base pairing will occur when the signal primer is hybridized to a second allele of the target nucleic acid, the difference in the efficiency of polymerase extension when the signal primer is hybridized to the two different alleles may be used to indicate which allele the target nucleic acid contains. When any one of multiple alleles may be present, multiple signal primers are employed in the analysis, each with a different potential mismatch at or near the 3' end. The signal primer which is most efficiently extended provides the identity of the allele (i.e., the identity of the nucleotide present in the target sequence being analyzed). For example, if a set of signal primers comprising A, G, C and T at the site of the allele to be identified is hybridized to the target of interest and extended, the identity of the allele will be the complement of the nucleotide in the signal primer which was most efficiently extended by the polymerase. For identification of the allele in a single reaction, multiple signal primers are present in the reaction, each with a separately detectable adapter sequence and reporter probe (i.e., the adapter tails of the signal primers differ and are detectable using reporter probes that are labeled with different fluorophores which can be distinguished individually from within the mixture of reporter probes).

More specifically, the signal primers of the invention are oligonucleotides which hybridize to the target sequence of interest and are extended by DNA polymerase during the amplification reaction. The nucleotide sequence of the signal primer is selected such that it hybridizes specifically to the target nucleic acid of interest with the majority of the signal primer bases pairing correctly in typical Watson-Crick fashion with the target. The nucleotide sequence of the signal primer at or near the 3' end is selected to discriminate between different alleles, SNPs or other variants of the target sequence. Accordingly, the signal primer contains a "diagnostic nucleotide" (defined above) at or near its 3' end. The diagnostic nucleotide permits analysis (e.g. detection or identification) of a particular allele in a selected target. The diagnostic nucleotide is chosen so that it forms a proper Watson-Crick base pair with the selected nucleotide variant of the intended target when the signal primer is hybridized to the target. In contrast, hybridization of the signal primer to an incorrect sequence variant will result in formation of a mismatch, rather than a Watson-Crick base pair, between the diagnostic nucleotide and the variant nucleotide of the (incorrect) target. Efficient signal primer extension will occur only when the diagnostic nucleotide participates in a proper Watson-Crick base pair with the variant nucleotide of the target. If the signal primer hybridizes to the incorrect sequence variant, the diagnostic nucleotide participates in a mismatch rather than a proper Watson-Crick pair, and extension of the signal primer is retarded. This difference in efficiency of signal primer extension arising from participation of the diagnostic nucleotide in a base pair or a mismatch with the target sequence facilitates discrimination between allelic or single nucleotide variants. As an example of how mismatches in the primer allow allele discrimination in amplification reactions, if a signal primer having a C residue at the diagnostic nucleotide position produces a high signal indicative of efficient extension of the signal primer, this indicates that the target allele is G. In contrast, low signal for the extended signal primer indicates that the target allele is not G. Use of a single signal primer to make the analysis allows identification of an allele if only one SNP is expected to occur in the target. If there may be multiple different alleles present at the same nucleotide position, a single signal primer will provide information on the presence or absence of the allele for which the signal primer is diagnostic. To identify the allele when multiple SNPs are possible, multiple signal primers containing A, T and G at the site of the SNP may be used to identify the allele in the target, i.e., the signal primer which produces the highest signal associated with signal primer extension product contains the nucleotide which is the complement of the SNP in the target. In the present invention, the potentially mismatched nucleotide of the signal primer is placed at the 3' terminus or about one to four nucleotide residues from the 3' terminus (i.e., at the N, N-1, N-2, N-3 or N-4 position).

It has been found that in many cases it is preferable to place a second mismatch in the sequence of the signal primer that is not directed to detection or identification of the allele of interest. The second, non-diagnostic mismatch often improves the level of discrimination between the SNPs being detected or identified and is preferably selected based on a region of the target sequence which is not expected to vary so that the non-diagnostic mismatch will occur regardless of the target allele being analyzed. The second mismatch may occur at any site within the signal primer that produces a positive effect on allele discrimination, but typically produces the greatest improvement when it is near the diagnostic nucleotide. This is typically within one to fifteen nucleotides from the diagnostic nucleotide, but preferably within about 1-5 nucleotides of the diagnostic nucleotide of the detector primer. The non-diagnostic mismatch may be placed either 5' or 3' of the diagnostic nucleotide in the signal primer. Applicants believe that the second, non-diagnostic mismatch has a positional effect rather than a general effect on the $T_m$ of the signal primer, based on the observation that as the non-diagnostic mismatch is moved away from the diagnostic mismatch its positive effect on allele discrimination diminishes. Those skilled in the art are capable of determining through routine experimentation the appropriate placement of the non-diagnostic mismatch in a signal primer by evaluating its effect on allele discrimination using the signal primer.

Although it is known that a mismatch in a shorter oligonucleotide will have a greater effect on hybridization than a mismatch in a longer oligonucleotide, allele discrimination using the signal primers of the invention cannot be attributed entirely to a $T_m$-associated hybridization effect. For example, moving the position of the diagnostic nucleotide away from the 3' end of the signal primer toward the center of the molecule substantially reduces discrimination. If the sole mechanism of discrimination between alleles was $T_m$-associated hybridization efficiency, this repositioning should increase rather than decrease allele discrimination.

When the signal primer forms a mismatch with the target at or near it's 3' end, the detection efficiency of the mismatched target is reduced. The accompanying reduction in signal upon detection of the extended signal primer (i.e., the amplification product or amplicon) indicates the presence or the identity of a SNP at the position in the target sequence at which the diagnostic mismatch with the signal primer occurred. If the signal primer comprises an adapter tail such that, when the complement of the adapter is synthesized as a result of extension of the signal primer, a signal change is produced then the extension products may be detected in real-time as amplification of the target occurs. This eliminates the additional steps of post-amplification detection of extension products. In isothermal amplification reactions such as SDA, a single mismatch at N-1 or N-2 in the signal primer in general may provide more efficient allele discrimination than a single mismatch at the 3' terminus. In the isothermal amplification methods of the present invention a mismatch on the signal primer in close proximity to the diagnostic nucleotide also results in excellent allele discrimination. The latter configuration therefore represents a preferred embodiment for signal primers of the invention.

In the above embodiments, the signal primer is typically hybridized to the target downstream from any primer which is extendible by polymerase such that extension of the second primer displaces the signal primer and any signal primer extension products which may be produced. Another embodiment uses signal primers with target binding sequences that are at least partially identical to the target binding sequence of an amplification primer (FIG. 4). Competitive hybridization between two oligonucleotides in an amplification/detection system has been described previously (U.S. Pat. No. 6,258, 546 herein incorporated by reference) for qualitative and quantitative detection of nucleic acids. This approach provides detection efficiency that is equal to or better than that of conventional signal primers that lie entirely between the amplification primers, while still maintaining the specificity derived from use of an internal probe. Overlap between the hybridization regions of the amplification and signal primers allows for flexibility in assay design and a reduction in overall amplicon length, with the resulting potential for enhanced amplification efficiency. This is important because flexibility in system design is necessary to avoid primer:primer interactions, restriction enzyme recognition sites, amplicon secondary structure and regions of excessively high G-C content. Overlap of the signal primer and an amplification primer may also enhance allelic discrimination by providing additional competition between closely related sequences for hybridization to the target sequence. In a conventional system containing two signal primers, each specific for one of two alleles at a given locus, and an upstream amplification primer, there is competition between the two signal primers for hybridization to the target sequence. Hybridization of the specific oligonucleotide is, however, thermodynamically favored, resulting in elevated signals for the specific allele. In a further embodiment of the invention, an increase in specific signal (or reduction in non-specific signal) may be expected when additional competition for hybridization of the signal primer to the target is provided by an overlapping amplification primer.

The applicants hypothesize that efficiency of allelic discrimination obtained with the signal primers of the invention are at least partially due to a kinetic effect. If a signal primer is not efficiently extended on a target to which it is hybridized (e.g., when it contains mismatches), it will be quickly displaced from the template by extension of the upstream (or overlapping) amplification primer. If the signal primer is efficiently extended, extension will occur before the signal primer is displaced from the target. That is, the upstream (or overlapping) amplification primer, (which is typically perfectly matched and efficiently extended) imposes a "time-limit" for extension on the signal primer. This is an improvement over methods of allelic discrimination that rely upon terminal or near-terminal mismatches in amplification primers. In such systems, the amplification primer in an isothermal reaction does not have a time-limit for extension imposed upon it by additional components of the isothermal amplification reaction or by thermocycling. Therefore, with sufficient time available, an imperfectly matched amplification primer may eventually be extended even when the extension reaction is inefficient. This phenomenon could impair the ability to discriminate between alleles when an amplification primer with a 3' terminal mismatch is employed in isothermal amplification reactions. In addition, the ability of amplification primers to correct a mismatch with the target may contribute to these observations. Amplification primers produce amplicons that are perfectly matched with the amplification primers that produced them, thus eliminating the basis of allelic discrimination. In contrast, such "correction" does not occur with signal primers.

Whether hybridization of the signal primer results in correct base-pairing or a mismatch at the diagnostic nucleotide position of the target being analyzed is determined by evaluating the relative efficiency of detector primer extension by DNA polymerase. This determination may be quantitative or qualitative. Signal primer extension is less efficient in the presence of a mismatch at or near the 3' end and more efficient when the entire 3' end is correctly base-paired with the target. That is, relatively more extended signal primer product is synthesized with correct base-pairing near the 3' terminus. According to the method of the invention, the extended signal primer is typically detected by means of its 5' adapter tail sequence. The adapter tail is copied during the course of amplification to generate a complementary oligonucleotide that may be detected by hybridization to a reported probe. The relative amount of signal generated by the reporter probe is correlated with the amount of extended signal primer in the reaction. Comparison of signals associated with different signal primer/reporter combinations indicates the relative efficiency of signal primer extension and permits discrimination of alternative alleles.

There are many techniques known in the art for determining the presence or amount of extended signal primer product produced in the amplification reaction. First, the extension products of the signal primer may be detected and/or quantified by their increased size, for example by separation from unextended detector primer by gel electrophoresis or by selectively capturing the extended signal primer on a solid phase. However, in the preferred embodiment the signal primers comprise a 5' adapter sequence that is detectable only when the signal primer has been extended and its complement synthesized during the course of the reaction. The signal primer compliment is detected by hybridization to a detectable reporter probe. One example of such detectable labels are fluorescent dyes which undergo changes in fluorescence polarization when the oligonucleotides to which they are linked have been hybridized to and extended on a target sequence. Methods employing changes in fluorescence polarization to detect hybridization and extension of a signal primer are described in U.S. Pat. No. 5,800,989; U.S. Pat. No. 5,593,867; and U.S. Pat. No. 5,641,633. These patents describe using changes in fluorescence polarization which occur when the signal primer becomes double-stranded (made possible by its successful extension on the target sequence) to detect target amplification. In the methods of the invention, changes in fluorescence polarization of a fluorescently-labeled reporter primer may be used to evaluate extension efficiency and to detect or identify a SNP in the target being amplified.

A second example of labels which undergo a detectable change in signal indicative of primer extension are fluorescent donor/quencher dye pairs. The quencher dye may also, but need not necessarily, be fluorescent. When the donor and quencher are in close proximity, fluorescence of the donor is quenched. As the dyes are moved farther apart, quenching is reduced and donor fluorescence increases. The use of such donor/quencher dye pairs in a variety of mechanisms for increasing the distance between the dyes in the presence of target for detection of target nucleic acids is described in U.S. Pat. No. 5,846,726; U.S. Pat. No. 5,691,145, and EP 0 881 302. Both the use of donor/quencher dye pairs in signal primer amplification systems and in extendible primer/probes for detection of unamplified or post-amplification targets are disclosed. In the present invention, the reporter probes of the invention may be labeled with donor/quencher dye pairs and employed for detection and/or identification of SNPs in the target as is known in the art.

As disclosed in the foregoing references, a variety of primer extension detection systems are known for use in essentially any nucleic acid amplification reaction. They are particularly well-suited to isothermal amplification reactions where they provide rapid, real-time detection of primer extension. In the methods of the present invention, signal primers may comprise adapter sequences that are detectable only upon successful extension of the signal primer. Preferred embodiments employ donor/quencher dye pairs to detect signal primer extension products. It will be apparent that, in addition to SDA, the signal primers of the invention may be adapted for use in other primer extension amplification methods (e.g., PCR, 3SR, TMA or NASBA). For example, the methods may be adapted for use in PCR by substituting PCR amplification primers and employing a strand displacing DNA polymerase which lacks 5'→3' exonuclease activity (e.g., Sequencing Grade Taq from Promega or exo⁻ Vent or exo⁻ Deep Vent from New England BioLabs) in the PCR. The signal primers hybridize to the target downstream from the PCR amplification primers. They are extended, displaced from the target and rendered double-stranded essentially as described for SDA. The single-stranded oligonucleotide comprising the complement of the signal primer 5' adapter sequence is generated by denaturing the double-stranded secondary amplification product, followed by hybridization of the reporter probe and polymerase extension to synthesize the complementary strand of the labeled reporter moiety in the reporter probe. As in SDA systems, synthesis of the complementary strand either directly or indirectly provides a change in the proximity of donor and quencher dyes and changes the degree of fluorescence quenching. An associated change in a fluorescence parameter, such as intensity, serves as an indication of target amplification.

For adaptation of the inventive methods to 3SR, TMA or NASBA, a 5'→3' exonuclease deficient reverse transcriptase with strand displacing activity is employed, with hybridization of the signal primer to the RNA target downstream of an amplification primer. In a reaction scheme similar to that previously described, the hybridized signal primer is 1) extended, and 2) displaced by extension of the upstream amplification primer. The displaced signal primer extension product is then made entirely double-stranded by hybridization and extension of the second amplification primer which contains an RNA polymerase promoter. The promoter sequence, which is located on the 5' tail of the second amplification primer, is made double-stranded by extension of the 3' end of the signal primer extension product. From the double-stranded promoter, RNA polymerase generates RNA copies complementary to the signal primer extension product. The 3' end of each RNA copy contains a sequence complementary to the adapter sequence of the signal primer. This sequence then hybridizes to a complementary region of the reporter probe. If the reporter probe is extendible, reverse transcriptase will extend the 3' end of the probe upon the RNA template to produce a reporter probe extension product. RNase H will then degrade the RNA strand of this heteroduplex, freeing the reporter probe extension product to hybridize with the second amplification primer containing the promoter sequence. Conversion of the promoter sequence to the double-stranded form will initiate a new round of RNA synthesis, yielding products that are complementary to the reporter probe extension product, including the full reporter moiety sequence. Hybridization of reporter probes to these RNA targets will cause the reporter moiety to unfold, producing signal as donor and quencher dyes are separated and quenching is reduced. In addition, the reporter probes will be extended upon the RNA target as described above and the cycle will be repeated.

If the reporter probes are not extendible (capped) the adapter sequence of the signal primer must be selected to contain sequences such that the complement of the adapter sequence will hybridize to the reporter moiety of the reporter probe. The reaction will proceed as described above, except that the capped reporter probes will not be extended and the RNA complements of the signal primer extension product will hybridize to the capped reporter probe (including the reporter moiety). Signal will be produced as the reporter moiety unfolds and quenching of donor fluorescence is relieved during hybridization.

For reduced background, it is preferred that the signal primers of the invention be used as described above, with the signal primer extension product being separated from the target sequence by displacement due to extension of the upstream amplification primer. However, it will be apparent that the amplification primers known for use in the various nucleic acid amplification reactions may themselves be used for hybridization of the reporter probe if the primers contain appropriate adapter sequences. In this embodiment, the adapter sequence of an SDA primer is located between the nickable restriction endonuclease site that drives SDA and the target binding sequence. SDA with this primer will produce an amplified product that contains at its 3' end a sequence complementary to the reporter probe. Binding of the reporter probe to this complementary sequence will produce signal as described above. For PCR and NASBA the amplification primers are modified by addition of a noncomplementary 5' tail as described above for the signal primer. In the case of NASBA, the primer lacking the RNA polymerase promoter is the primer modified with the 5' adapter sequence. During PCR and NASBA, complements of the adapter-containing primer extension products are produced as described above for the signal primers. These complementary sequences are made single-stranded either by heat denaturation (PCR) or enzymatic digestion of RNA template (RNase H in NASBA), and the single-stranded complement then binds to reporter probe as described above for signal primers. The use of amplification primers as signal primers eliminates the need for the additional signal primer in the reaction, but because background may be higher in this embodiment the sensitivity of the assay may be decreased.

In other alternative embodiments, the signal primers of the invention may be used in non-amplification based assay formats to detect target sequences. In a first non-target amplification embodiment, the 3' single-stranded target binding sequence of the signal primer hybridizes to the 3' end of the target sequence such that the 5' adapter sequence forms a 5' overhang. The target sequence functions as a primer for synthesis of a strand complementary to the signal primer using a polymerase to extend the target sequence using the 5' overhang as a template. If the target binding sequence of the signal primer hybridizes to only a portion of the target sequence, the target sequence also forms a 5' overhang and the signal primer may be similarly extended using the 5' overhang of the target as a template. Alternatively, the signal primer may be non-extendible as synthesis of a copy of the target sequence is not required in this embodiment of the invention. In either case, the complement of the adapter sequence of the signal primer is synthesized. Upon separation of the two strands, the complement of the signal primer adapter sequence in the target will hybridize to the 3' end of the reporter probe, rendering the labeled reporter moiety double-stranded upon polymerase extension of the recessed 3' end of the adapter sequence complement. An advantage of this embodiment over the reaction described in U.S. Pat. No. 5,866,336 is that use of the overhang allows synthesis of the complement of the adapter sequence in a single extension step rather than two. That is, the complement of the adapter sequence is appended directly to the original target, thus allowing target detection without requiring amplification. In a second preferred non-target amplification embodiment of the invention the signal primer is hybridized to an internal sequence of the target with an additional primer hybridized upstream to displace it (commonly referred to as a "bumper" primer). The signal primer and bumper primer are extended such that the signal primer extension product is displaced from the target sequence. A second pair of primers are hybridized to the extension product and extended such that the downstream primer extension product contains the complement of the adapter sequence and is displaced from the signal primer extension product by extension of its bumper primer. The reporter probe hybridizes to the complement of the adapter sequence and the adapter sequence is extended as described herein to synthesize the complement of the reporter moiety. Because this is an isothermal reaction which depends on strand displacement to separate complementary strands, extension of the first bumper primer renders the target double-stranded and unable to participate in any further reaction steps. Although a copy is generated and displaced, this is not considered target amplification because the copy represents a subsequence of the original target which is detected as an indication of the presence of the target and only one copy of the subsequence is generated per original target sequence.

The foregoing disclosure primarily relates to preferred embodiments in which the reporter moiety is labeled with a fluorescent donor/quencher dye pair and synthesis of the complement of the reporter moiety is detected by an increase in fluorescence. This label system allows synthesis of the complement to be detected in real-time and/or in a homogeneous assay (i.e., without separation of the label prior to detection). However, other labels useful in the invention will be apparent to those skilled in the art. For example, a single fluorescent label may be employed on the reporter moiety with detection of a change in fluorescence polarization in the presence of the complement of the reporter moiety (see U.S. Pat. No. 5,593,867). Non-fluorescent labels are also useful. For example, the reporter moiety may be labeled with a lipophilic dye and contain a restriction site which is cleaved in the presence of the complement of the reporter moiety (see U.S. Pat. No. 5,550,025). Alternatively, the reporter probe may be radiolabeled and the products resulting from synthesis of the complement of the reporter moiety may be resolved by electrophoresis and visualized by autoradiography. Immunological labels may also be employed. A reporter probe labeled with a hapten can be detected after synthesis of the complement of the reporter moiety by first removing unreacted reporter probe (for example by adapter-specific capture on a solid phase) and then detecting the hapten label on the reacted reporter probe using standard chemiluminescent or calorimetric ELISAs. A biotin label may be substituted for the hapten and detected using methods known in the art.

The label indicating the presence of the complement of the reporter moiety may be detected at a selected endpoint in the reaction. However, because oligonucleotides with increased distance between the donor and the quencher are produced concurrently with hybridization and primer extension, the label may also be monitored as the reaction is occurring, i.e., in "real-time". This homogeneous, real-time assay format can be used to provide semi-quantitative or quantitative information about the initial amount of target present. For example, the rate at which the label (e.g., fluorescence intensity) changes during the reaction (either as part of target amplification or in non-amplification detection methods) is an indication of initial target levels. As a result, when more initial copies of the target sequence are present, the label more rapidly reaches a selected threshold value (i.e., shorter time to positivity). In addition, the rate of change in the label during the course of the reaction is more rapid in samples containing higher initial amounts of target than in samples containing lower initial amounts of target. These or other measurements as are known in the art may be made as an indication of the presence of target or as an indication of target amplification. The initial amount of target is typically determined by comparison of the experimental results to results for known amounts of target.

Many donor/quencher dye pairs known in the art are useful in preferred embodiments of the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/quencher pair is not critical. For energy transfer quenching mechanisms it is only necessary that the emission wavelengths of the donor fluorophore overlap the excitation wavelengths of the quencher, i.e., there must be sufficient spectral overlap between the two dyes to allow efficient energy transfer, charge transfer or fluorescence quenching. P-(dimethyl aminophenylazo) benzoic acid (DABCYL) is a non-fluorescent quencher dye which effectively quenches fluorescence from an adjacent fluorophore, e.g., fluorescein or 5-(2'-aminoethyl)aminonaphthalene (EDANS). Certain donor/quencher pairs are exemplified above and in the following Examples, however, others will be apparent to those skilled in the art and are also useful in the invention. Any dye pair which produces fluorescence quenching in the reporter probes of the invention are suitable for use in the methods of the invention, regardless of the mechanism by which quenching occurs. Terminal and internal labeling methods are also known in the art and may be routinely used to link the donor and quencher dyes at their respective sites in the reporter probe.

Example 1

Strand Displacement Amplification reactions containing signal primers according to the invention were run essentially as described in U.S. Pat. No. 5,547,861 for detection of a synthetic target sequence. A first reaction contained $10^6$ copies of the target sequence, SDA amplification primers appropriate for amplification of the synthetic target sequence, 100 nm of a signal primer according to the invention comprising a target binding sequence specific for the target and a 5' tail sequence identical to the 3' sequence of a reporter probe, and 200 nm of the reporter probe. The sequence of the reporter probe contained an RERS in the 5' region flanked by fluorescein and Rhodamine X (Rox) such that fluorescence of fluorescein was quenched when the RERS was intact. The sequences of the signal primer and reporter probe (shown in the 5' to 3' direction) are shown below. The target binding sequence is shown in italics, the 5' adapter sequence of the signal primer and the identical 3' sequence of the reporter probe are underlined and the RERS of the reporter probe is bolded.

```
Signal Primer (SEQ ID NO:1):
CCAAAATGACAGCTTCTGATGGAATGACTCACTGAGTTGGAACGT

Reporter Probe (SEQ ID NO:2):
(fluorescein)TACCTCGAGT
(rox)GCAGCCAAAAGACAGCTTCTGATGGAA
```

Figure 5:
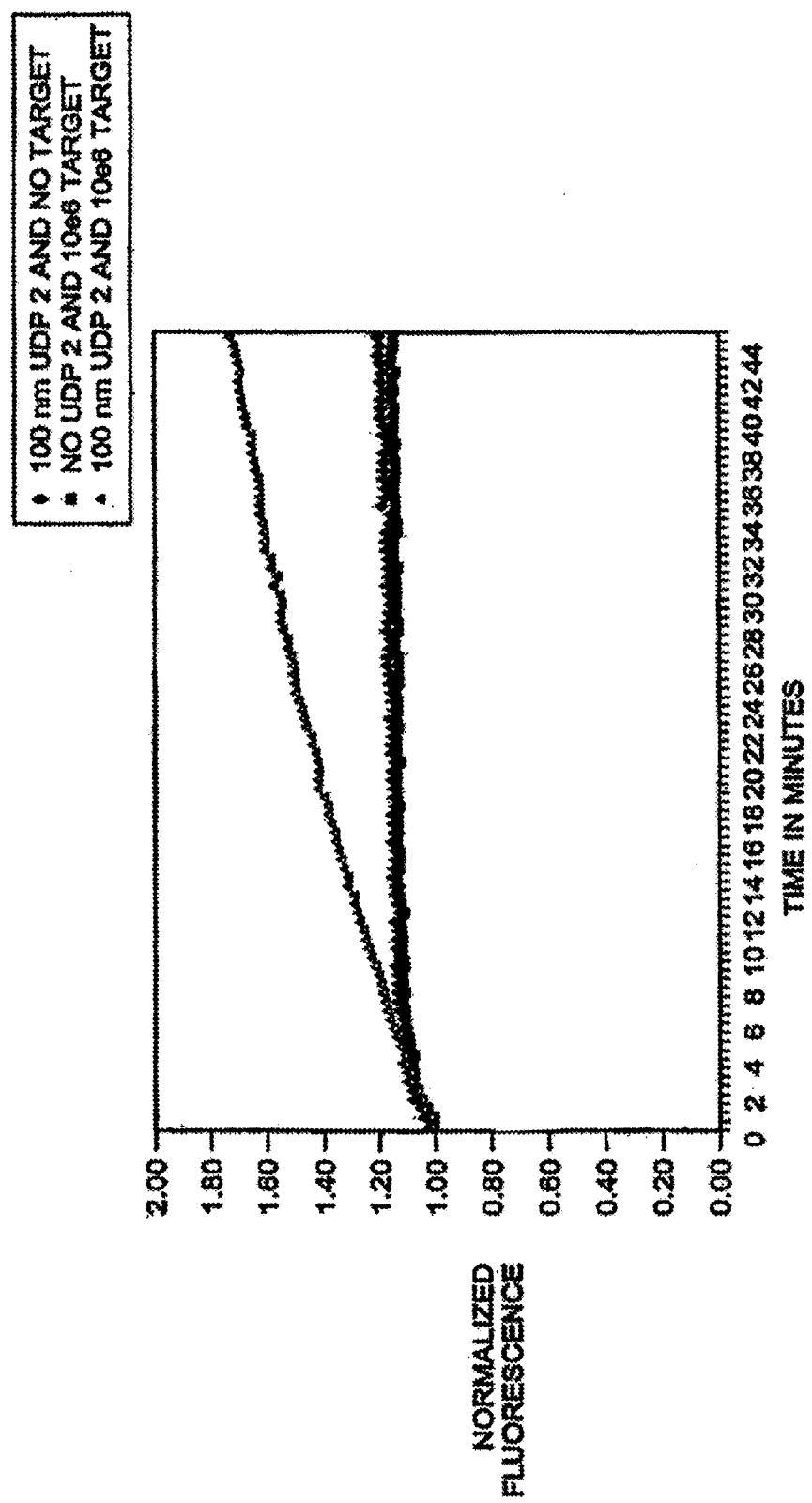
FIG. 5 illustrates the results of Example 1.

A second reaction contained no target and the same signal primer as in the first reaction. A third reaction was a control reaction which contained only $10^6$ copies of target and the reporter probe (i.e., no signal primer). Fluorescein fluorescence was detected in real-time during the amplification reactions. As shown in FIG. 5, donor fluorescence remained low and constant in the absence of target, indicating quenching of fluorescence throughout the reaction due to failure of the RERS of the reporter probe to be converted to double-stranded form and cleaved. In the absence of signal primer donor fluorescence also remained quenched throughout the amplification reaction. In the presence of target, signal primer and reporter probe, however, donor fluorescence was initially low but increased during the time course of the amplification reaction as the RERS of the reporter probe was converted to double-stranded form and cleaved to reduce the extent of fluorescence quenching. These results demonstrate that the signal primers and reporter probes of the invention can be used to detect a nucleic acid target sequence by monitoring changes in the extent of fluorescence quenching.

In a similar experiment, 0 and 250 copies of cloned HIV target DNA were detected using a variety of signal primers in combination with one of two reporter probes, each having the same sequence but labeled with different donor/quencher dye pairs. The sequences of the signal primers and reporter probes are shown in the 5' to 3' direction below. The target binding sequence is shown in italics, the 5' adapter sequence of the signal primer and the identical 3' sequence of the reporter probe are underlined and the RERS of the reporter probe is bolded.

fluorescence generated by a particular reporter probe/signal primer combination and the more efficient the detection of amplified products. Both reporter probes worked well in combination with all signal primers for detection of the HIV target, although performance was generally not as good as for reporter probes containing hairpin reporter moieties. However, linear reporter probes such as these are shorter than reporter probes containing secondary structures and are therefore easier to synthesize with higher yield. Higher MOTA values were obtained using the fluorescein-dabcyl reporter probe, suggesting that this dye pair may have a higher quenching efficiency.

Example 2

SDA reactions were prepared to contain the different signal primers shown in Example 1, either 0 or 5,000 copies of the cloned HIV target, and a reporter probe. The sequence of the reporter probe was as follows:

```
(dabcyl)TAGTGCCCGAGCACT(rox)GAAAGACGTTAGCCACCATACGGAT      (SEQ ID NO:16, TBD9)
```

SEQ ID NO:16 contains a BsoBI RERS in the single-stranded loop of a hairpin structure at the 5' end. The SDA reactions contained 500 nM SDA amplification primers, 50 nM bumper primers, and 200 nM each signal primers and reporter probes. Rhodamine fluorescence was monitored during amplification. For each signal primer/reporter probe combination rhodamine fluorescence increased in the presence of target during the amplification reaction. In the absence of target rhodamine fluorescence remained low throughout the

```
Signal Primers:
GAAAGACGTTAGCCACCATACGGATACCCCTTTTCTTTTAAAATTGTG         (SEQ ID NO:3, UA1)

GAAAGACGTTAGCCACCATACGGATACCCCTTTTCTTTTAAAATTGTGGATG     (SEQ ID NO:4, UA2)

GAAAGACGTTAGCCACCATACGGATACCCCTTTTCTTTTAAAATT            (SEQ ID NO:5, UA3)

GAAAGACGTTAGCCACCATACGGATACCCCTTTTCTTTTAAAATTG           (SEQ ID NO:6, UA3.1)

ACGTTAGCCACCATACGGATACCCCTTTTCTTTTAAAATTGTG              (SEQ ID NO:7, UA4)

ACGTTAGCCACCATACGGATACCCCTTTTCTTTTAAAATTGTGGATG          (SEQ ID NO:8, UA5)

ACGTTAGCCACCATACGGATACCCCTTTTCTTTTAAAATT                 (SEQ ID NO:9, UA6)

ACGTTAGCCACCATACGGATACCCCTTTTCTTTTAAAATTG                (SEQ ID NO:10, UA6.1)

AGCCACCATACGGATACCCCTTTTCTTTTAAAATTGTG                   (SEQ ID NO:11, UA7)

AGCCACCATACGGATACCCCTTTTCTTTTAAAATTGTGGATG               (SEQ ID NO:12, UA8)

AGCCACCATACGGATACCCCTTTTCTTTTAAAATT                      (SEQ ID NO:13, UA9)

AGCCACCATACGGATACCCCTTTTCTTTTAAAATTG                     (SEQ ID NO:14, UA9.1)

Reporter Probes                                          (SEQ ID NO:15)
(fluorescein)TGCCCGAGT(dabcyl)GAAAGACGTTAGCCACCATACGGAT (fluorescein)TGCCCGAGT(rox)GAAAGACGTTAGCCACCATACGGAT
```

Figure 6A:
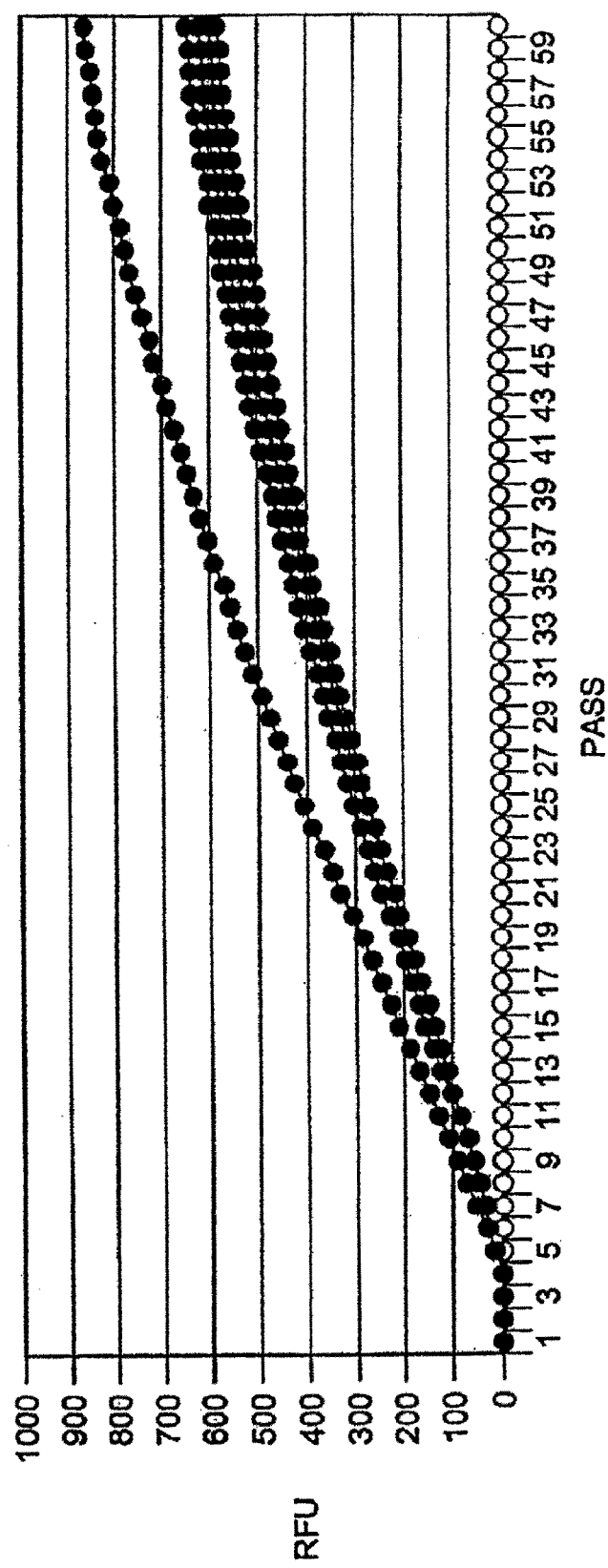
FIG. 6A and FIG. 6B illustrate the results of Example 2.

The signal primers differed in length and $T_m$ of the target binding sequence and of the reporter binding sequence. Fluorescein fluorescence was monitored during amplification. To compare the reporter probe/signal primer combinations, results were expressed as the area under the fluorescence curve or "MOTA". The more area under the curve, the more reaction. The results of one of the reactions are shown in FIG. 6A, for signal primer SEQ ID NO:3, with the multiple curves representing replicate samples. Results indicated that the length and $T_m$ of the adapter sequence did not significantly affect assay performance. However, the $T_m$ of the target binding sequence of the signal primer influenced signal generation, with signal primers comprising longer target binding sequences performing better than those with shorter target binding sequences.

The experiment was repeated using three different reporter probes, including SEQ ID NO:16. The additional reporter probes were as follows:

(fluorescein)TAGTGCCCGAGCACT(dabcyl)<u>ACGTTAGCCACCATACGGAT</u>  (SEQ ID NO:17, TBD10)

(fluorescein)TAGTGCCCGAGCACT(dabcyl)<u>AGCCACCATACGGAT</u>  (SEQ ID NO:18, TBD11)

Figure 6B:
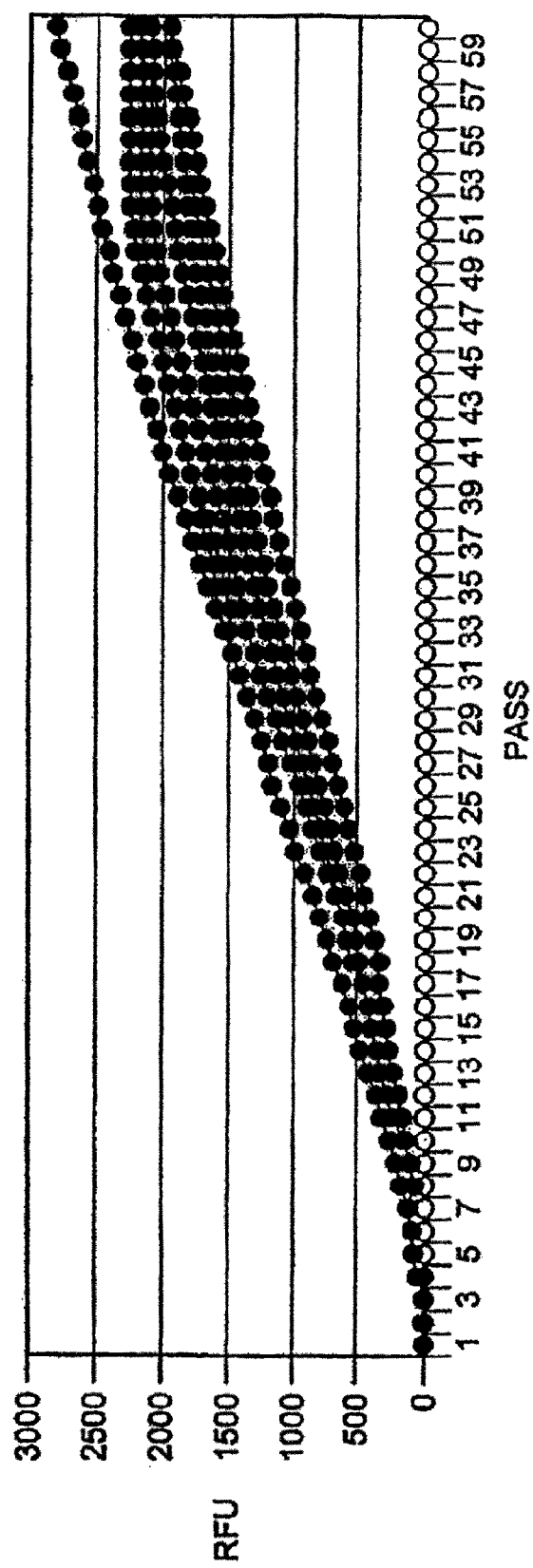

In this experiment the concentration of the upstream amplification primer was reduced to 100 mM. Amplification was performed in the presence of either 0 or 250 copies of target DNA. Reactions containing target showed a rapid increase in fluorescein fluorescence after as little as 5 min. of incubation. In contrast, reactions without target exhibited low fluorescein fluorescence throughout the reaction period. Results for a reaction containing SEQ ID NO:8 and SEQ ID NO: 17 are shown in FIG. 6B, with the multiple curves representing replicate samples. The reporter probe/signal primer combinations SEQ ID NO:16/SEQ ID NO:4 and SEQ ID NO:17/SEQ ID NO:8 produced similar MOTA values (62,147 and 66,051 respectively), whereas the SEQ ID NO:18/SEQ ID NO:12 combination was less efficient (MOTA=49,879) suggesting less efficient hybridization and conversion due to the shorter probe and primer length.

Example 3

In this experiment a reporter probe comprising a hairpin and a nickable rather than cleavable BsoBI RERS was tested in SDA. The reporter probe had the following sequence (SEQ ID NO:19, TBD13.1):

(fluorescein)TAGTGCTCGGGCACT(dabcyl)<u>GAAAGACGTTAGCCACCATACGGAT</u>

This reporter probe was used with SEQ ID NO:4 as the signal primer in the amplification reaction. A mean MOTA value of 48,000 was obtained in the presence of 250 copies of HIV target DNA, compared with a score of less than 150 from negative controls. The lower MOTA score observed as compared to reporter probe SEQ ID NO:16, which has the same 3' tail sequence may be due to inefficient priming of the polymerase off the short oligonucleotide that is left after nicking of the BsoBI site. Performance of the reaction may be enhanced by increasing the length of the hairpin to stabilize this oligonucleotide and provide a larger region for binding of the polymerase.

Example 4

In this experiment SDA was performed using a reporter probe containing a G-quartet structure and an RERS as the reporter moiety. This reporter probe had the following sequence (SEQ ID NO:20, TBD14):

An increase in fluorescein fluorescence was observed during the course of amplification of 250 copies of HIV target DNA. No such increase in fluorescence was observed in the absence of target.

Example 5

In this experiment, sequence variations within the human $\beta_2$AR gene and its upstream 5' untranslated region were used as targets for the development of six different adapter-mediated SNP detection systems according to the method of the invention. SDA systems comprising two bumper primers, two amplification primers and two allele-specific signal primers were designed for each of six SNP sites (−654, −367, −47, +46, +491 and +523) (Table 1, FIG. 7). Within each system, the two signal primers comprised identical sequences except for the diagnostic nucleotide that was positioned one base upstream from the 3' terminus (N-1). In each SDA system, the same pair of adapter sequences was appended to the 5' ends of the signal primers to permit detection using a common pair of universal reporter probes. The variant position of the signal oligonucleotide contained either adenosine (A), cytosine (C), guanine (G) or thymine (T). For the purposes of this study, "wild-type" allele (or allele A) refers to the sequence illustrated in GeneBank (Accession # M15169) while "mutant" (or allele B) represents the alternative nucleotide (SNP). $\beta_2$AR target sequences containing allele A and/or allele B of each of the six targeted SNPs were cloned in to pUC 19 from pooled human genomic DNA.

SDA analysis of the six SNPs was carried out as follows. In brief, cloned $\beta_2$AR SNPs targets ($1\times10^5$ copies per reaction) in a common SDA buffer were denatured for 5 min at 95° C. and cooled to room temperature. The denatured target was added to Priming Microwells containing SDA primers, bumper primers, the two allele-specific signal primers and universal reporter probes (Table 1). The target-primer mixture was incubated for 5 min at room temperature. Priming Microwells were then heated at 72° C. for 10 min to denature any non-specific hybridization that might have occurred. At the same time, Amplification Microwells containing dried Bst DNA polymerase and BsoBI restriction enzyme were pre-equilibrated at 52° C. One hundred microliters of the target-primer mix was transferred to the Amplification Microwells, sealed and incubated at 52° C. in a ProbeTec™ ET System. The final reactions contained; 24.5 mM potassium phosphate (fluorescein)GGTTGGCTCGAGGTTGGT(dabcyl)<u>GAAAGACGTTAGCCACCATACGGAT</u>

(pH 7.6), 11 mM Bicine, 82 mM potassium hydroxide, 12.5% dimethylsulfoxide (DMSO), 5 mM magnesium acetate, 10 µg acetylated bovine serum albumin, 100-500 nM upstream primer, 100-500 nM downstream primer, 50 nM bumper primers, 100-250 nM signal primers, 150-500 nM reporter probes, 0.1 mM deoxyadenosine triphosphate, 0.1 mM deoxyguanosine triphosphate, 0.1 mM thymidine triphosphate, 0.5 mM 2'-Deoxycytidine 5'-O-(1-Thiotriphosphate) S-isomer, approximately 120 units of Bst DNA polymerase and 300 units of BsoBI restriction enzyme.

Specific amplification products were detected by monitoring the change in fluorescence intensity associated with the hybridization of a reporter probe to the complement of the appropriate signal primer, the subsequent extension of the signal primer complement and cleavage of the resultant double stranded product. For each well, one fluorescein (FAM) (mutant signal) and one rhodamine (ROX) (wild-type signal) reading was made every minute during the course of the reaction. The FAM and ROX fluorescence readings for each sample were plotted over 60 minutes. For SNP reactions containing wild-type target only, there was a significant increase in ROX fluorescence, over time, compared to a minor increase FAM. In contrast, the fluorescence profile was reversed for samples containing mutant target DNA. In samples containing both wild-type and mutant DNA target, fluorescence increased in both optical ranges, indicating the presence of both alleles in the sample.

Figure 8:
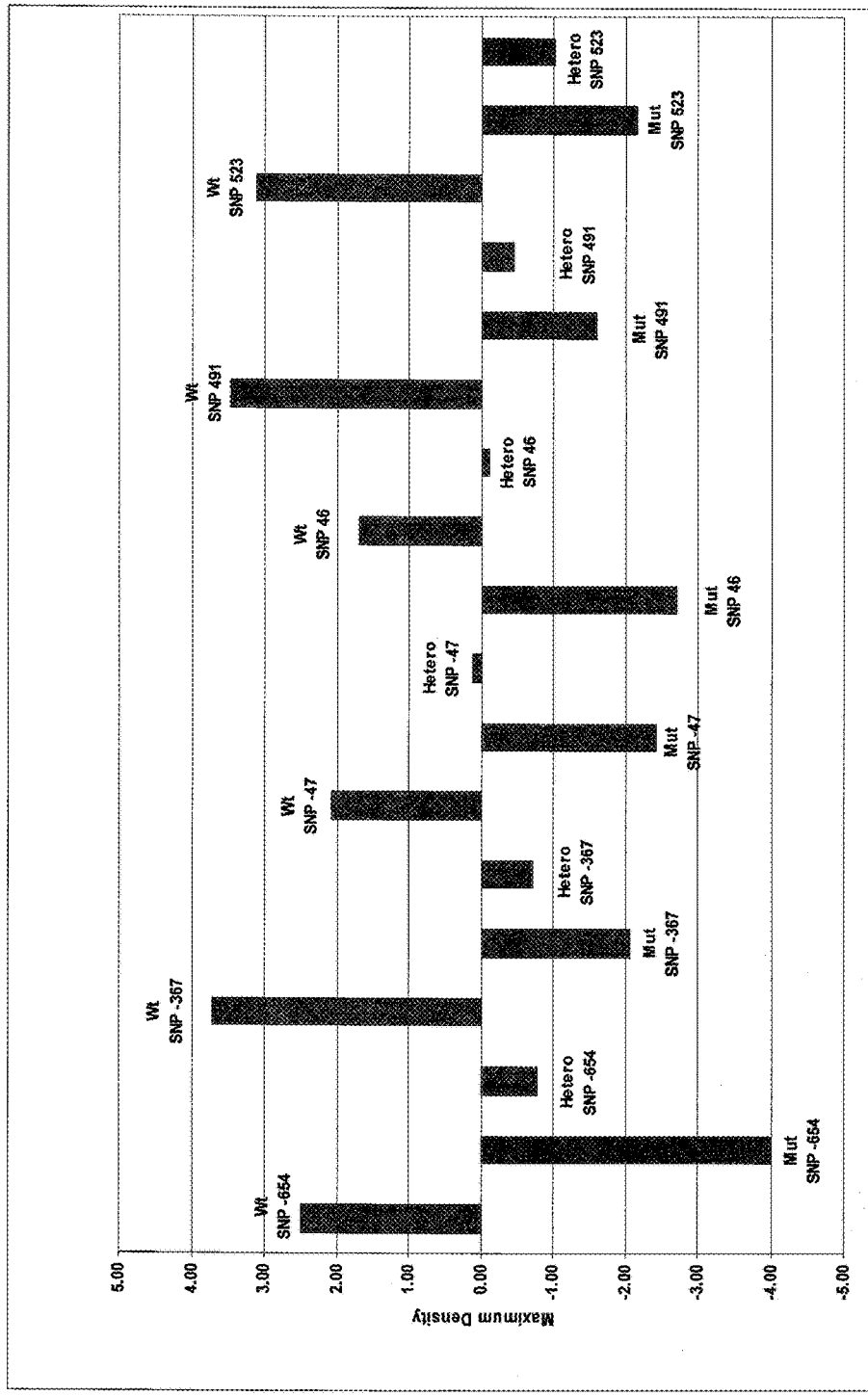
FIG. 8 illustrates the results obtained in Example 5 from 6β2AR SNP assays using the Maximum Density algorithm.
Figure 9:
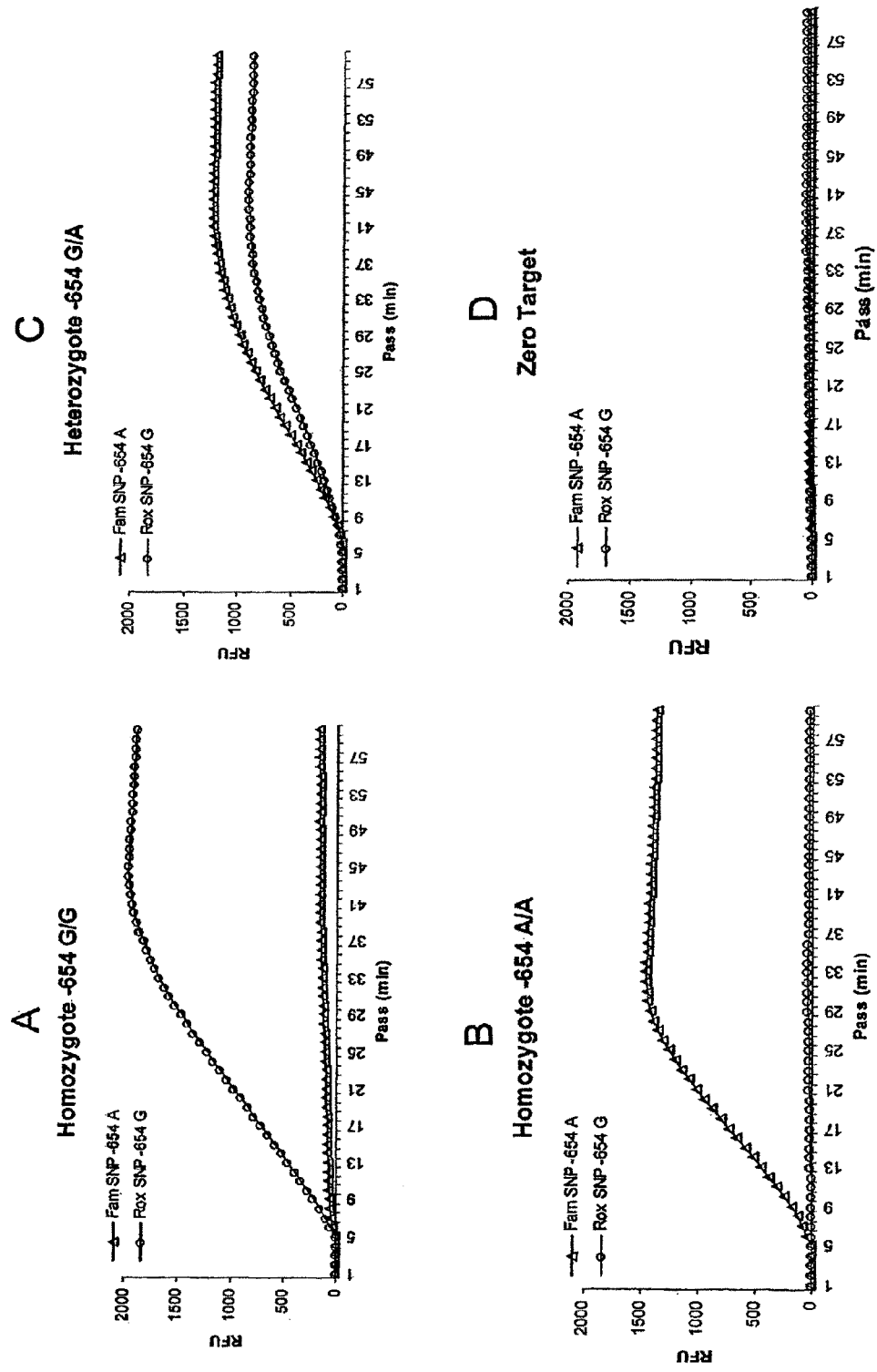
FIGS. 9A-D illustrate the amplification curves obtained in Example 5 from the assay for the −654 β2AR SNP.

The allele specific fluorescence signals were analyzed using the SNP V2.6. The Maximum Density metric (derived from the ratio of ROX and FAM signals (ln(ROX/FAM)) was used to determine which allele was present in the sample. High positive values (typically >1.0) indicated allele A (homozygous wild-type), low negative values (typically <−1.0) indicated allele B (homozygous mutant) and values close to zero (typically −1.0 to +1.0) indicated the presence of a mixture of both allele A and B (heterozygous) (FIG. 8).

FIGS. 9A-D show the results obtained from genotyping cloned $\beta_2AR$ targets containing the −654 SNP. In each case, SDA results correlated with those based on sequence analysis of the cloned DNA target. Signal primers with perfect complementarity to the target sequence were preferentially extended and detected over those that contained a mismatch at the position of the diagnostic nucleotide.

Example 6

Sequence variation at two SNP sites within the same amplified target region of the $\beta_2AR$ gene was detected by designing a single pair of SDA primers that spanned the region of interest together with signal primers that were specific for each of the individual SNPs. As in Example 5, the diagnostic nucleotides in the signal primers were positioned at the penultimate (N-1) 3' residue. The amplification primer, bumper primer, signal primer and reporter probe sequences are listed in Table 1. Use of common amplification primers allows the simultaneous identification of multiple sequence alleles or sequence variations in close proximity. According to the method of the invention, a single reaction under one set of amplification conditions (buffer, enzyme concentrations, temperature, etc.) can provide a convenient, reliable, and inexpensive method for identifying multiple sequence alleles.

Single nucleotide variations at amino acids 164 (nucleotide +491) and amino acid 175 (nucleotide +523) of the $\beta_2AR$ gene were detected and identified using common amplification primers, bumper primers and reporter probes in conjunction with allele-specific diagnostic signal primers that were specific for the two targeted SNPs. As in Example 5, the term wild-type refers to the sequence recorded in GeneBank Accession # M15169 while mutant represents the alternative allele. For the +491 nucleotide position, the wild-type allele is a C, whereas the mutant allele is a T at this position. This nucleotide change results in a threonine to isoleucine amino acid change. For the +523 nucleotide position, the wild-type allele is a C, whereas the mutant allele is an A at this position.

SDA was generally performed as described in Example 5. The final concentrations of components in each 100 µL reaction were 101 mM bicine, 82 mM KOH, 24.5 mM KiPO$_4$ (pH 7.6), 5.0 mM MgOAc, 0.1 mM each dTTP, dGTP, DATP, 0.5 mM dCTPαS, 10 µg acetylated BSA, approximately 300 units of BsoBI, approximately 120 units of Bst polymerase. The target for amplification consisted of a cloned double stranded DNA sequence containing the wild-type or mutant nucleotides at positions 491 and 523 of the $\beta_2AR$ gene.

SDA reactions were carried out at 52° C. in the presence of $10^5$ copies of target. Control reactions contained no target DNA. For each well, one FAM (detects mutant signal) and one ROX (detects wild-type signal) reading was made every minute during the course of the reaction. Fluorescent readings for each sample type were plotted over 60 minutes. For both SNP assays, in reactions containing wild-type target only there was a significant increase in ROX fluorescence over time compared to a relatively minor increase FAM signal. In contrast, the fluorescence profile was reversed for samples containing mutant target DNA. In the sample containing both wild-type and mutant DNA, fluorescence increased in both optical ranges indicating the presence of both alleles in the sample. Maximum Density results obtained from cloned $\beta_2AR$ SNP targets for SNP +491 and +523 systems are shown in Table 2. These results confirm the feasibility of the method of the invention for detecting multiple allelic variations within a region of DNA that is spanned by two amplification primers.

Example 7

This example demonstrates the detection of six SNPs within the human $\beta_2AR$ gene according to the method of the invention. The disclosed primers and assay systems permit the identification of the five most common $\beta_2AR$ haplotype pairs (Drysdale et al., Proc. Natl. Acad. Sci., 2000; 97: 10483-10488). Haplotype analysis has become increasingly important in the emerging field of pharmacogenomics in which phenotypes typically involve the interaction of several loci throughout the genome. Multiple SNP detection is important for circumstances in which individual SNPs have poor predicative power. The advantage of the disclosed invention is the ability to genotype multiple loci using common amplification conditions (buffer, enzymes, temperature, etc.), thereby providing an improved workflow and ease of use over existing methods. The primer, adapter and probe sequences of the six SNP assays are listed in Table 1. In each assay system the diagnostic nucleotide of the signal primers was positioned at the penultimate (N-1) 3' residue, thereby reducing non-specific priming and enhancing discriminatory power.

Single nucleotide variations in the 5' upstream and coding sequences of the $\beta_2AR$ gene at nucleotides −654, −367, −47, +46, +491 and +523 of the $\beta_2AR$ were detected essentially as described in Example 2. The target for amplification consisted of two cloned double stranded DNA sequences of approximately ~1.5 kb that spanned all six targeted SNP loci of the $\beta_2AR$ gene. The individual clones were genotyped by sequence analysis. To create a heterozygous target pool for each SNP, equal mixtures of wild-type and mutant clones were prepared. Reactions were carried out at 52° C. in the presence of $10^5$ copies of target as described in Example 5. Control reactions contained no target DNA. For each well, one FAM (mutant signal) and one ROX (wild-type signal) reading was made every minute during the course of the 60 minute reaction time. For SDA reactions containing only wild-type target for a given locus, there was a significant increase in ROX fluorescence over time compared to a relatively minor increase FAM signal. In contrast, the fluorescence profile was reversed for samples containing only mutant target DNA. In samples containing both wild-type and mutant target for a specific locus, fluorescence increased in both optical ranges, indicating the presence of both alleles in the sample.

As described in Example 5, the ratio of ROX to FAM fluorescence was used to determine the nucleotide base present at each SNP locus. Results from all six SNP sites were combined to provide a haplotype for each of the cloned targets. In both cases, the specific alleles at each locus and overall haplotypes agreed with DNA sequence analysis (Table 3).

Example 8

Modified SDA primers were designed for the –367 $\beta_2$AR SNP such that the target hybridization region of the amplification primers overlapped that of the signal primers (Table 1, FIG. 4). Competitive hybridization between two oligonucleotides in an amplification/detection system has been described previously (U.S. Pat. No. 6,258,546 herein incorporated by reference) for the qualitative and quantitative detection of nucleic acids. The extensive overlap between the amplification and signal primers in the –367 system provided for an overall shorter amplicon than is possible with conventional designs. This is an important attribute because the sequence around this SNP is approximately 78% G-C rich, which is far beyond the 60% cutoff suggested for most amplification methods. The ability to reduce amplicon size has the potential to provide a more robust amplification reaction and does not appear to impair analytical sensitivity. Importantly, the design of amplification and signal primers that almost completely overlap limits the amount of sequence available for non-specific interactions, which inevitably inhibit the efficiency of amplification and detection.

Figure 10:
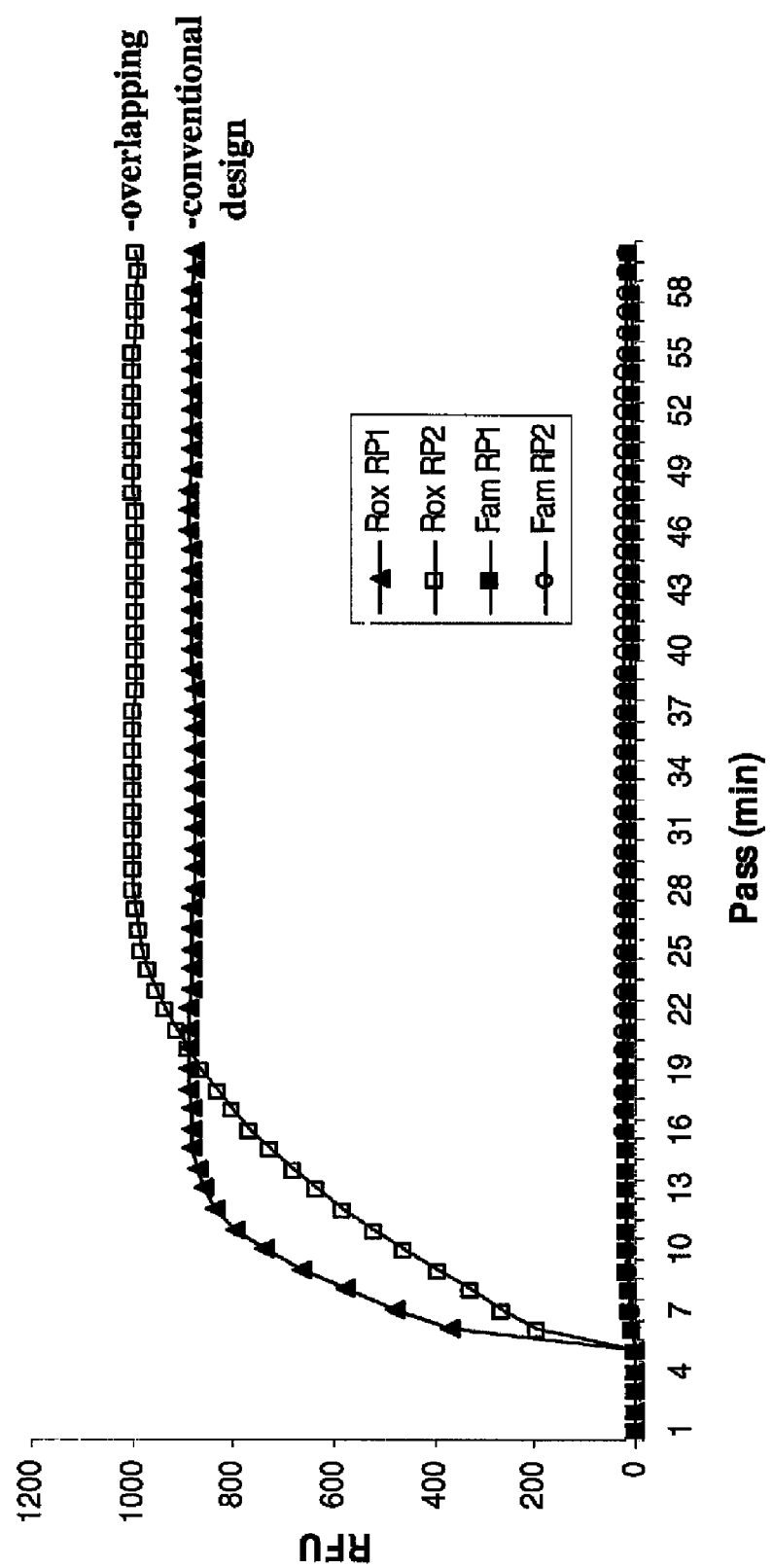
FIG. 10 illustrates a comparison of signals obtained in Example 8 using conventional and overlapping signal primers in the detection of the −367 β2AR SNP.

Apart from inclusion of the new SDA primer in one of the reaction mixtures, amplification conditions were the same as those described in Example 5. Reactions were carried out at 52° C., in the presence of $10^6$ copies of oligonucleotides containing target allele A (homozygous), allele B (homozygous) or a mixture of alleles A and B (heterozygous). Control reactions contained no target DNA. FIG. 10 shows the amplification curves for the conventional –367 SNP assay and those obtained with an overlapping primer design. Good discrimination of alleles A and B was obtained with both SDA systems.

Example 9

The experiment described in Example 5 was repeated for the –654 SNP assay except that the two signal primers were modified to include additional mismatches towards the 3' terminus of the target binding sequence (FIG. 11). The artificially created mismatches were introduced 3 bases from the 3' terminus (N-3 position), and 2 bases upstream of the diagnostic nucleotide (N-1). Each of the two allele-specific signal primers was used in conjunction with the other SDA primers employed in the –654 SNP assay system described in Example 5. SDA reactions were performed containing $10^4$ or $10^6$ copies of synthetic target oligonucleotides representing allele A (homozygous), allele B (homozygous), or a mixture of oligonucleotides representing alleles A and B (heterozygous). Results showed that signal intensities obtained using primers containing the additional non-diagnostic mismatch with the target sequence were lower than those achieved with the original primer design. However, allelic discrimination with the modified signal primers was vastly improved (Table 4). For reactions containing just the allele A target, a strong ROX signal was obtained while the FAM signal was efficiently suppressed. The opposite was true in reactions containing just the allele B target. When a mixture of alleles A and B was present, signals were obtained with both the ROX and FAM channels.

This example illustrates that an artificially created mismatch in the signal primer of the inventive method can be used to enhance allelic discrimination. Such mismatches may be located upstream or downstream of the diagnostic nucleotide and serve to destabilize the base pairing at the 3' end of the signal primer, thereby reducing the efficiency of polymerase extension. This may be of particular importance in systems designed to discriminate SNPs in highly G-C rich DNA in which base pairing and base stacking interactions are particularly strong.

Example 10

This example illustrates the use of non-diagnostic mismatches in amplification primers to modify or eliminate restriction enzyme sites that would preclude detection by SDA. In the SDA systems described in the previous examples, amplification is achieved through the coordinated activity of Bst DNA polymerase and the restriction enzyme, BsoBI. Hybridization of a target nucleic acid containing a BsoBI recognition sequence to a complementary primer would result in the formation of a double stranded substrate for enzymatic cleavage (FIG. 3A, B). Alternatively, hybridization of a primer upstream of a BsoBI recognition sequence site and extension of the primer by polymerase through the restriction site would also result in formation of a cleavable substrate. Were either of these scenarios to occur, the target sequence would be unable to serve as a template for SDA. For most diagnostic applications this limitation on SDA system design is easily overcome by careful selection of target sequences that lack recognition sites for the SDA enzyme(s). For SNP analysis, however, it represents a more challenging problem because with these assays there is no latitude in selection of the target sequence. To overcome this problem, SDA systems can be designed with deliberate mismatches with the target in either the bumper or amplification primer hybridization sequences (FIGS. 3A and 3B). In the SNP –367 system described in the previous examples, a mismatch was synthesized in the left amplification primer target binding sequence 3 bases from the 5' end of the target hybridization region (Table 1). This creates a C:A mismatch in the BsoBI recognition sequence, thereby preventing cleavage of the primer:target hybrid. Similarly, in the +46, +491, and +523 systems, mismatches were synthesized in the middle of the left bumper sequence, preventing restriction by the BsoBI enzyme.

Example 11

This example illustrates detection of sequence variations using signal primers that hybridize to opposite strands of the target DNA. This approach can help modify or eliminate intra- or inter-molecular interactions (e.g., hairpin formation or primer dimers) that could reduce the efficiency of polymorphism detection. In the SDA systems described in the above examples, pairs of signal primers to detect a specific polymorphism were designed with target hybridizing regions that were identical except for the diagnostic nucleotide at the 3' end of the sequence. When this approach was used for the design of signal primers to the +46 SNP, the signal primer for allele B was found to form a strong intra-molecular secondary structure (i.e., a hairpin) which impaired detection of the allele (FIG. 12A, B). To alleviate this interaction, signal primers were designed for the +46 $\beta_2$AR SNP such that the target hybridization regions complimented opposite strands of the target sequence either side of the SNP site. One signal primer, designed to identify allele A, overlapped the target hybridization region of the forward amplification primer while a second signal primer, designed to identify allele B, overlapped the hybridization region of the reverse amplification primer (FIG. 12A). In order to reduce intra- and inter-molecular interactions even further, the 5' adapter tails of the signal primers used to detect alleles A and B were swapped (i.e, the adapter sequence for the ROX reporter probe was appended to the signal primer for allele B, while the adapter sequence for the FAM reporter was appended to the signal primer for allele A). Because the sequence around the +46 SNP locus is approximately 68% G-C rich, this region is prone to severe intra- and inter-molecular interactions which are known to impair amplification and/or detection. The ability to develop an assay system with signal primers on opposing strands therefore provides important flexibility in assay optimization.

SDA was generally performed as described in Example 5. Reactions were carried out at 52° C., in the presence of $10^5$ copies of cloned target containing target allele A (homozygous), allele B (homozygous) or a mixture of alleles A and B (heterozygous). Control reactions contained no target DNA. The Maximum Density metric was used to determine the identity of the nucleotide present at the +46 SNP locus. In order to standardize the results, data from the conventional signal primer system were analyzed using the ratio ln(ROX/FAM) while data from the system based on opposing signal primers were analyzed using the ratio ln(FAM/ROX). This reflected the reversal of the optics for alleles A and B caused by swapping of the signal primer tail sequences. With the conventional assay system, signals for allele B were suppressed. In contrast, with the opposing signal primer design, signals were obtained for both allele A and allele B, with good discrimination between the two. This example illustrates that signal primers designed to opposite strands of a SNP locus can be used to eliminate strong base pairing and base stacking interactions that may inhibit amplification and/or detection.

Example 12

Six SNPs within the $\beta_2$AR gene were detected directly in human blood samples using the adapter-mediated detection system of the invention. SDA was performed as described in Example 7 with some modifications. Whole blood, from 8 individuals, was mixed with SDA components for a final 100 µL reaction volume which contained 101 mM Bicine, 82 mM KOH, 24.5 mM KiPO$_4$ (pH 7.6), 5.0 mM MgOAc, 0.1 mM each dTTP, dGTP, dATP, 0.5 mM dCTPαS, 10 µg acetylated BSA, approximately 300 units of BsoBI, and 120 units of Bst polymerase. For each reaction, 20 µL blood was mixed directly with SDA amplification buffer, heated for 5 minutes at 100° C., centrifuged at 10,000×g for 1 minute, and transferred directly into the SDA reaction. The final reaction mixture contained 13% blood by volume. Results from analysis of the 6 SNP loci by SDA were compared with direct sequencing of PCR products and with those obtained from blood that was processed according to a commercial DNA purification procedure (QIAamp® DNA Blood Mini Kit). For each assay system, SDA reactions containing wild-type target only exhibited a significant increase in ROX fluorescence over time compared to a minor increase FAM signal. In contrast, The reverse was true for samples containing mutant target DNA. In samples containing heterozygous target, fluorescence increased in both optical channels indicating the presence of both alleles in the sample. Data were collected and analyzed as described in Example 5 and the results of SDA-based analysis of all 6 SNP loci are summarized in Table 5. In all cases, the SDA-based analysis was in complete concordance with sequence data. Table 6 shows representative data comparing SDA SNP detection with DNA sequencing analysis for nucleotide −654 of the $\beta_2$AR gene.

The ability of the assays to amplify successfully directly from blood without sample processing was unexpected. There is extensive literature to suggest that blood which has not undergone significant manipulation and from which the nucleic acid has been isolated and purified, inhibits most amplification procedures. These results suggest that the SDA-based systems of the invention are likely to have a distinct advantage in terms of workflow and time-to-result over procedures that require minutes to hours of DNA purification prior to nucleic acid amplification and detection.

Example 13

SNPs within the $\beta_2$AR gene were analyzed according to the method of the invention using target nucleic acid from expressed buccal swab samples. Buccal swabs from 4 individuals were expressed in 1 ml of SDA buffer which was then heated for 5 min in a boiling water bath and centrifuged for 1 min at 10,000×g to pellet cellular debris. The denatured target DNA in the supernatant was then mixed with additional reaction components to provide a final 100 µL reaction volume containing: 101 mM Bicine, 82 mM KOH, 24.5 mM KiPO$_4$ (pH 7.6), 5.0 mM MgOAc, 0.1 mM each dTTP, dGTP, DATP, 0.5 mM dCTPαS, 10 µg acetylated BSA, approximately 300 units of BsoBI and 120 units of Bst polymerase. Data were collected and analyzed as described in Example 5. SDA results were compared with direct sequence analysis of PCR amplified target. SDA reactions containing wild-type target only showed a significant increase in ROX fluorescence over time compared to a minor increase FAM signal. The reverse was true for samples containing mutant target DNA. In samples containing heterozygous target DNA fluorescence increased in both optical ranges, indicating the presence of both alleles in the sample. The results of SDA-based analysis for the −654 locus from buccal swab samples were in complete concordance with sequence data (Table 6). Analysis of SNPs directly from buccal swabs provides a distinct advantage in terms of workflow and time-to-result over procedures that require minutes to hours of DNA purification prior to nucleic acid amplification and detection. The non-evasive nature buccal swab collection, as well as the lack of sample processing, makes this an attractive sample type for genotyping and haplotype analysis.

Example 14

The $\beta_2$AR −654 SNP locus was analyzed according to the method of the invention with target DNA recovered from first-catch urine. SDA was performed as described in Example 5 with some modifications. Two milliliters of urine from each of 4 individuals were centrifuged at 1000×g to concentrate any human cells present. The supernatant was decanted and the cellular pellet was resuspended in 50 μL TE and 250 μL SDA buffer. The cell suspension was then heated for 5 min at 100° C. to lyse the cells and denature the target nucleic acid. One hundred and twenty microliters of the target-buffer mixture were added to a Priming Microwell as described in Example 5. Amplification was then initiated by transferring the contents of the Priming Microwell to an Amplification Microwell. Each final 100 μL reaction volume contained: 101 mM Bicine, 82 mM KOH, 24.5 mM KiPO4 (pH 7.6), 5.0 mM MgOAc, 0.1 mM each dTTP, dGTP, dATP, 0.5 mM dCTPαS, 10 μg acetylated BSA and approximately 300 units of BsoBI and 120 units of Bst polymerase. The results of SDA-based SNP analysis were compared to those obtained by direct sequencing of genomic DNA obtained from the blood of the individuals who donated the urine. In all cases, the SDA-based results were in complete concordance with the sequence data. Representative data for the −654 SNP of the $\beta_2$AR gene are shown in Table 6. SDA reactions containing wild-type target only showed a significant increase in ROX fluorescence over time compared to relatively minor increase in FAM signal. The reverse was true for samples containing mutant target DNA. In the sample containing both wild-type and mutant DNA, fluorescence increased in both optical ranges, indicating the presence of both alleles in the sample.

As with the ability to genotype directly from buccal swabs (Example 13), the use of urine as a sample type has distinct advantages in terms of ease of collection. In conjunction with this, the minimal sample processing that is required for the disclosed procedure offers advantages in terms of workflow and time-to-results over amplification methods that require minutes to hours of DNA purification prior to nucleic acid amplification and detection. The ready availability of urine samples and minimal sample processing requirements makes them an attractive sample type for genotyping and haplotype analysis. Other sample types (e.g., fingernails, hair, blood drops, sputum) may also be appropriate for analysis of sequence variations according to the method of the invention with little or no sample processing.

Example 15

SNP −654 within the $\beta_2$AR gene was analyzed according to the method of the invention, using target nucleic acid from an expressed skin swab sample. A skin swab from subject D in Table 6 was expressed in 0.4 mL of SDA buffer which was then heated for 5 min in a boiling water bath. The denatured target DNA was then mixed with additional reaction components to provide a final 100 μL reaction volume containing: 101 mM Bicine, 82 mM KOH, 24.5 mM KiPO4 (pH 7.6), 5.0 mM MgOAc, 0.1 mM each dTTP, dGTP, dATP, 0.5 mM dCTPαS, 10 μg acetylated BSA, SDA primers, bumper primers, two allele-specific signal primers, two universal reporter probes and approximately 300 units of BsoBI and 120 units of Bst polymerase. Data were collected and analyzed as described in Example 5. Fluorescence increased in both optical ranges (ROX and FAM), indicating the presence of both alleles in the sample. These results agreed with those obtained by direct sequencing of genomic DNA obtained from the blood and with other SDA-based genotyping results obtained from blood, buccal swabs and urine (Table 6). Analysis of SNPs directly from skin swabs provides a distinct advantage in terms of workflow and time-to-result over procedures that require minutes to hours of DNA purification prior to nucleic acid amplification and detection. The non-evasive nature of skin swab collection, as well as the lack of sample processing, makes this an attractive sample type for genotyping and haplotype analysis.

TABLE 1

SDA Primers

```
SNP 654
Bumper primers
mLB       AGT GTG CAT GTC GGT GA (SEQ ID NO: 23)
RB        GAG GCA CGC ACA TAC AG (SEQ ID NO: 24)
Amplification Primers
LP        ACC GCA TCG AAT GAC TGT CTC GGG TGT GTC TCA GTG TCT
          (SEQ ID NO: 25)
RP        CGA TTC CGC TCC AGT CTT CTC GGG ATA CAC CCT GGC AG
          (SEQ ID NO: 26)
Signal Primers
AD2       ACG TTA GCC ACC ATA CGG ATT GTG GTT CGG TAT AAG TaT GA
          (SEQ ID NO: 27)
mC1D2     AGC TAT CCG CCA TAA GCC ATT GTG GTT CGG TAT AAG TgTAA
          (SEQ ID NO: 28)

SNP 367
Bumper primers
LB        TCC AGG GAG CAG TTG (SEQ ID NO: 29)
RB        AAC TTT CGG CCA ATG (SEQ ID NO: 30)
Amplification Primers
mLP1      CGA TTC CGC TCC AGA CTT CTC GGG CGa CCG GGC CAG C
          (SEQ ID NO: 31)
RP2       CGA TTC CGC TCC AGA CTT CTC GGG CTC GCC CTC CTT CT
          (SEQ ID NO: 22)
Signal Primers
AD5       ACG TTA GCC ACC ATA CGG ATC CTC CTT CTC CTG GG
          (SEQ ID NO: 21)
mAD2      AGC TAT CCG CCA TAA GCC ATC CCT CCT TCT CCT GAG
          (SEQ ID NO: 32)
```

TABLE 1-continued

```
SNP 47
Bumper primers
LB      ACA GCC GCT GAA TGA G (SEQ ID NO: 33)
RB      TGG CAG GTA AGC GCA CT (SEQ ID NO: 34)
Amplification Primers
LP      CGA TTC CGC TCC AGA CTT CTC GGG tCC GCA GAG CC
        (SEQ ID NO: 35)
mRP     ACC GCA TCG AAT GAC TGT CTC GGG aGC GCC TCA G
        (SEQ ID NO: 36)
Signal Primers
AD4     ACG TTA GCC ACC ATA CGG ATT CCG TGG GTC CGC CCG
        (SEQ ID NO: 37)
MAD     AGC TAT CCG CCA TAA GCC ATC CGT GGG TCC GCC TG
        (SEQ ID NO: 38)

SNP 46
Bumper primers
mLB     TGG GGC AAt CCG GGA A (SEQ ID NO:39)
RB      CAC ACC TCG TCC CCT T (SEQ ID NO:40)
Amplification Primers
LP      CGA TTC CGC TCC AGA CTT CTC GGG TGG CAG CGC CTT CTT
        (SEQ ID NO: 41)
RP      ACC GCA TCG AAT GAC TGT CTC GGG GTG GTC CGG CGC AT
        (SEQ ID NO: 42)
Signal Primers
AD4     ACG TTA GCC ACC ATA CGG ATC TTG CTG GCA CCC AAa AG
        (SEQ ID NO: 43)
mAD4    AGC TAT CCG CCA TAA GCC ATC TTG CTG GCA CCC AAa GG
        (SEQ ID NO: 44)

SNP 491
Bumper prirmrs
LB      AAT AAG GCa CGG GTG (SEQ ID NO: 45)
RB      TTG GTT CGT GAA GAA GT (SEQ ID NO: 46)
Amplification Primers
LP      CGA TTC CGC TCC AGA CTT CTC GGG TGG TGT GGA TTG TGT C
        (SEQ ID NO: 47)
RP      ACC GCA TCG AAT GAC TGT CTC GGG TCT CAT TGG CAT AGC A
        (SEQ ID NO: 48)
Signal Primers
WTAD    ACG TTA GCC ACC ATA CGG ATA ATG GGC AAG AAG GAG GT
        (SEQ ID NO: 49)
MTAD    AGC TAT CCG CCA TAA GCC ATA ATG GGC AAG AAG GAG AT
        (SEQ ID NO: 50)

SNP 523
Bumper primers
LB      AAT AAG GCa CGG GTG (SEQ ID NO: 45)
RB      TTG GTT CGT GAA GAA GT (SEQ ID NO: 46)
Amplification Primers
LP      CGA TTC CGC TCC AGA CTT CTC GGG TGG TGT GGA TTG TGT C
        (SEQ ID NO: 47)
RP      ACC GCA TCG AAT GAC TGT CTC GGG TCT CAT TGG CAT AGC A
        (SEQ ID NO: 48)
Signal Primers
WTAD    AGC TAT CCG CCA TAA GCC ATA CAG ATG CAC TAG TAC CG
        (SEQ ID NO: 51)
MTAD    AGC TAT CCG CCA TAA GCC ATA CAG ATG CAC TAG TAC AG
        (SEQ ID NO: 52)
```

Reporter Probes
```
TBD10.2 D/R
        (Dabcyl)-TAG CGC CCG AGC GCT-(Rox)-ACG TTA GCC ACC ATA
          CGG AT (SEQ ID NO: 53)

AltD6.9 F/D
        (Fam)-AGT TGC CCC GAG GCA ACT-(Dabcyl)-AGC TAT CCG CCA
          TAA GCC AT (SEQ ID NO: 54)
```

Sequences complementary to the target DNA in the amplification and signal primers are underlined.
The diagnostic nucleotide within the signal primers is underlined twice and shown in bold face type.
Non-diagnostic mismatches with the target sequence in the signal primers, amplification primers and bumper primers are shown in lowercase.
BsoBI recognition sequences are italicized.
Mutated BsoBI recognition sequences are boxed.
Sequences forming the complementary stem of a hairpin structure in the reporter probes are shown in bold-face type.

TABLE 2

Maximum Density of 2 SNP Detection within a Single Amplified Target Sequence.

| Cloned Target | WT | MT | WT/MT | Negative |
|---|---|---|---|---|
| SNP 491 | 3.67 | −1.59 | −0.92 | indet |
| SNP 523 | 3.51 | −1.88 | −0.55 | indet |

TABLE 3

SDA haplotyping results match DNA sequence analysis

| Nucleotide: | −1023 | −709 | −654 | −468 | −406 | −367 | −47 | −20 | +46 | +79 | +252 | +491 | +523 | | | | |
|---|---|---|---|---|---|---|---|---|---|---|---|---|---|---|---|---|---|
| alleles: | G/A | C/A | G/A | G/C | C/T | C/T | C/T | T/C | A/G | C/G | G/A | C/T | C/A | Ca | AA | As | HL |
| Haplotype | | | | | | | | | | | | | | | | | |
| 1 | A | C | G | C | C | T | T | T | A | C | G | C | C | 0.7 | 25.0 | 12.5 | 10.0 |
| 2 | A | C | G | G | C | C | C | C | G | G | G | C | C | 48.3 | 6.3 | 10.0 | 26.7 |
| 3 | G | A | A | C | C | T | T | T | A | C | G | C | C | 0.7 | 0.0 | 0.0 | 0.0 |
| 4 | G | C | A | C | C | T | T | T | A | C | G | C | C | 33.0 | 29.7 | 45.0 | 40.0 |
| 5 | G | C | A | C | C | T | T | T | G | C | G | C | C | 1.4 | 0.0 | 0.0 | 0.0 |
| 6 | G | C | G | C | C | T | T | T | G | C | A | C | A | 13.2 | 31.3 | 30.0 | 13.3 |
| Nucleotide: | −1023 | −709 | −654 | −468 | −406 | −367 | −47 | −20 | +46 | +79 | +252 | +491 | +523 | | | | |
| Haplotype of cloned target: | | ↓ | | ↓ | ↓ | | ↓ | | | | ↓ | ↓ | | | | | |
| 2 | | | G | | C | C | | | G | | | C | C | by SDA | | | |
| 2 | | C | G | G | C | C | C | C | G | G | A | C | C | by sequencing | | | |
| 4 | | | A | | | T | T | | A | | | C | C | by SDA | | | |
| 4 | | C | A | C | C | T | T | T | A | C | G | C | C | by sequencing | | | |

TABLE 4

Maximum Density of the effect of non-diagnostic mismatches in signal primers

| Samples | Urine B | Urine C | Urine D | Urine E | water |
|---|---|---|---|---|---|
| AD/mAD | 2.77 | 3.02 | −0.23 | −1.27 | indet |
| AD2/mAD2 | 3.37 | 3.41 | −0.16 | −3.01 | indet |
| Genotype | G/G | G/G | G/A | A1A | indet |

Diagnostic mismatch primers

AD1  5'-ACG TTA GCC ACC ATA CGG ATT GTG GTT CGG TAT AAG TCT GA-3'  (SEQ ID NO:55)

mAD1 5'-AGC TAT CCG CCA TAA GCC ATT GTG GTT CGG TAT AAG TCT AA-3'  (SEQ ID NO:56)

Non-diagnostic Mismatch primers

AD2  5'-ACG TTA GCC ACC ATA CGG ATT GTG GTT CGG TAT AAG TaT GA-3'  (SEQ ID NO:27)

mAD2 3'-AGC TAT CCG CCA TAA GCC ATT GTG GTT CGG TAT AAG TgT AA-3'  (SEQ ID NO:28)

In each signal primer, the diagnostic nucleotide is located 1 base from the 3' end (N-1 position).
Lower case letters indicate the non-diagnostic mismatched nucleotides.
Underlined sequences hybridize to the target nucleic acid.
indet = indeterminate

TABLE 5

Haplotyping of Individuals from Blood

| Blood | −654 | −367 | −47 | 46 | 491 | 523 | Haplotype |
|---|---|---|---|---|---|---|---|
| SNP 2.6 Maximum Density | | | | | | | |
| A | 0.3 | −1.9 | −2.7 | −0.1 | 3.71 | 0.23 | |
| B | 3.2 | 3.2 | 2.5 | −2.9 | 3.78 | 3.36 | |
| C | 3.2 | −0.2 | 0.1 | −2.9 | 3.75 | 0.19 | |
| D | 0.2 | −2.0 | −2.8 | −0.1 | 3.61 | 0.15 | |
| E | −3.0 | −2.0 | −3.0 | 1.9 | 3.74 | 3.46 | |
| F | 3.3 | −0.2 | 0.2 | −2.8 | 3.71 | 0.19 | |
| G | 0.2 | −0.1 | 0.1 | 0.1 | 3.68 | 3.4 | |
| H | 3.4 | 3.8 | 2.5 | −2.3 | 3.66 | 3.66 | |
| SNP Genotype | | | | | | | |
| A | G/A | T | T | A/G | C | C/A | 4/6 |
| B | G | C | C | G | C | C | 2/2 |
| C | G | C/T | C/T | G | C | C/A | 2/6 |
| D | G/A | T | T | A/G | C | C/A | 4/6 |
| E | A | T | T | A | C | C | 4/4 |
| F | G | C/T | C/T | G | C | C/A | 2/6 |

TABLE 5-continued

Haplotyping of Individuals from Blood

| Blood | -654 | -367 | -47 | 46 | 491 | 523 | Haplotype |
|---|---|---|---|---|---|---|---|
| G | G/A | C/T | C/T | A/G | C | C | 2/4 |
| H | G | C | C | G | C | C | 2/2 |

TABLE 6A

Genotyping of the -654 B$_2$AR locus From Matched Samples

| | Subject | | | |
|---|---|---|---|---|
| Sample type | A | B | C | D |
| Blood (processed) | G/G | G/G | G/A | A/A |
| Blood | G/G | G/G | G/A | A/A |
| Buccal Swab | G/G | G/G | G/A | A/A |
| Urine | G/G | G/G | G/A | A/A |

TABLE 6A-continued

Genotyping of the -654 B$_2$AR locus From Matched Samples

| | Subject | | | |
|---|---|---|---|---|
| Sample type | A | B | C | D |
| Skin Swab | | | G/A | |
| Sequencing | G | G | G/A | A |

TABLE 6B

Maximum Density Values from Geneotyping of the B$_2$AR Locus in Matched Samples

| | Subject | | | |
|---|---|---|---|---|
| Sample type | A | B | C | D |
| Blood (processed) | 3.23 | 3.23 | 0.17 | -3.00 |
| Blood | 3.18 | 3.16 | -0.13 | -2.49 |
| Buccal Swab | 3.40 | 3.43 | -0.30 | -6.47 |
| Urine | 4.40 | 3.00 | -0.10 | -1.30 |
| Skin Swab | | | -0.30 | |

What is claimed is:

1. A method for detecting the presence or absence of at least one single nucleotide variation in at least one of target nucleic acids in a sample, comprising:
    a) obtaining a sample comprising target nucleic acids, wherein at least one of the target nucleic acids is suspected to contain at least one single nucleotide variation;
    b) selecting at least one signal primer comprising a 5' portion and a 3' portion, wherein said 3' portion of the at least one signal primer comprises at least one target binding sequence that specifically hybridizes to the at least one single nucleotide variation of 3' portion of said at least one target nucleic acid;
    c) selecting hybridization conditions such that the at least one signal primer hybridizes to its corresponding complementary sequence in the at least one of target nucleic acids that is suspected to contain the at least one single nucleotide variation, wherein said 5' portion of the at least one signal primer does not hybridize to a sequence in the at least one of target nucleic acids and a complement of at least part of said 5' portion of the at least one signal primer hybridizes to a 3' end of a reporter probe;
    d) mixing said at least one signal primer with the target nucleic acids and at least one amplification primer under the selected hybridization conditions so that said at least one amplification primer hybridizes to a region of said at least one of target nucleic acids that is upstream of a region of said at least one target nucleic acid hybridized to said 3' portion of said at least one signal primer, and wherein said at least one amplification primer and said at least one signal primer are extended under the selected hybridization conditions if the at least one signal primer does not form a mismatch with the 3' portion of said at least one of target nucleic acids;
    e) hybridizing a nucleic acid sequence to an extended portion of said at least one signal primer and synthesizing a complement of said at least one signal primer;
    f) hybridizing said complement of said at least one signal primer to at least one reporter probe comprising a label, wherein said at least one reporter probe does not hybridize to the at least one of the target nucleic acids but hybridizes to at least a portion of 5' portion of said complement of said at least one signal primer, and
    g) detecting a hybridized complex formed by said complement of said at least one signal primer and said at least one reporter probe, wherein the presence of the label of said at least one reporter probe on said hybridized complex indicates that the at least one single nucleotide variation is present in the at least one of target nucleic acids in said sample.

2. The method of claim 1, wherein said at least one signal primer comprises an identical 5' adapter sequence.

3. The method of claim 1, wherein said at least one reporter probes is used for detection of said single nucleotide variation in said at least one of target nucleic acids.

4. The method of claim 1, wherein said at least one signal primer comprise a diagnostic nucleotide which is one base to four bases from the 3' terminus of the at least one signal primer.

5. The method of claim 1, wherein said at least one signal primer comprises a diagnostic nucleotide at the 3' terminal end of the at least one signal primer.

6. The method of claim 4, further comprising creating artificial mismatches at one or more nucleotides of said at least one signal primer, wherein the artificial mismatches are created at one or more locations within five nucleotides from the diagnostic nucleotide.

7. The method of claim 1, wherein said sample is selected from the group consisting of blood, urine, buccal swabs, skin, fingernail, sputum, and hair.

8. The method of claim 1, wherein said at least one single nucleotide variation is associated with predisposition to an infectious or a non-infectious disease, with prediction of therapeutic efficacy or with a disease state selected from the group consisting of inherited disorders, acquired disorders and infectious disorders.

9. The method of claim 1, wherein said sample comprises genomic DNA.

10. A method for detecting at least one single nucleotide variation in a target nucleic acid in an amplification reaction comprising:
    a) obtaining a sample suspected to contain at least one target nucleic acid containing at least one single nucleotide variation;
    b) forming a mixture by mixing said sample with a signal primer comprising a 3' target binding sequence that specifically hybridizes the at least one single nucleotide variation of said at least one target nucleic acid and a 5' adapter sequence that does not hybridize to said at least one target nucleic acid such that the adapter sequence produces a 5' overhang;
    c) extending the signal primer in the mixture and producing an extension product if the at least one target nucleic acid is present in said sample;
    d) hybridizing an amplification primer to the extension product and extending the amplification primer so that a complement of the adapter sequence is synthesized if the at least one target nucleic acid is present in said sample;
    e) hybridizing a labeled reporter probe comprising a reporter moiety to the complement of the adapter sequence, whereby a double-stranded reporter moiety is produced if the at least one target nucleic acid is present in said sample; and
    f) detecting the double-stranded reporter moiety, wherein the presence of the double-stranded reporter moiety is an indication of the presence of said at least one single nucleotide variation in said at least one target nucleic acid if the at least one target nucleic acid is present in said sample.

11. A method for detecting at least one single nucleotide variation in a target nucleic acid, comprising:
    a) collecting a sample suspected to contain said target nucleic acid;
    b) mixing the sample and a signal primer comprising a 3' target binding sequence that specifically hybridizes to the at least one single nucleotide variation of said target nucleic acid and a 5' adapter sequence that does not hybridize to said target nucleic acid such that the adapter sequence produces a 5' overhang, wherein the signal primer hybridizes to the target nucleic acid only if the at least one single nucleotide variation is present in the target nucleic acid;

c) synthesizing a complement of the adapter sequence by extension if the at least one single nucleotide variation is present in the target nucleic acid;

d) hybridizing a labeled reporter probe comprising a reporter moiety to the complement of the adapter sequence, whereby a double-stranded reporter moiety is produced if the at least one single nucleotide variation is present in the target nucleic acid, and e) detecting the double-stranded reporter moiety, wherein the presence of the double-stranded reporter moiety is an indication of the presence of the at least one single nucleotide variations in said target nucleic acid.

* * * * *

UNITED STATES PATENT AND TRADEMARK OFFICE
CERTIFICATE OF CORRECTION

PATENT NO.        : 8,323,929 B2                                          Page 1 of 1
APPLICATION NO.   : 12/419737
DATED             : December 4, 2012
INVENTOR(S)       : Sha-Sha Wang et al.

It is certified that error appears in the above-identified patent and that said Letters Patent is hereby corrected as shown below:

In the Specification
Column 3, line 53, "generates signal" should read --generates a signal--.
Column 3, line 61, "species has provided" should read --species have provided--.
Column 4, line 26, "match one" should read --match of one--.
Column 9, line 12, "create an" should read --create a--.
Column 10, line 26, "double stranded" should read --double-stranded--.
Column 11, line 13, "product are produced" should read --product is produced--.
Column 12, line 53, "displacement produces" should read --displacement produce--.
Column 20, line 61, "primers are" should read --primers is--.
Column 22, line 27, "Invention are" should read --Invention is--.
Column 27, line 20, "reading was" should read --reading were--.
Column 28, line 23, "reading was" should read --reading were--.
Column 57, line 14, "variation of" should read --variation of said--.
Column 57, line 48, first occurrence of "portion of" should read --portion of said--.
Column 57, line 61, "probes is used" should read --probe is used--.
Column 57, line 64, "primer comprise" should read --primer comprises--.
Column 60, line 7, "nucleotide variations" should read --nucleotide variation--.

Signed and Sealed this
Eleventh Day of November, 2014

Michelle K. Lee
*Deputy Director of the United States Patent and Trademark Office*